United States Patent
Xue et al.

(10) Patent No.: US 11,085,016 B1
(45) Date of Patent: *Aug. 10, 2021

(54) METHOD FOR SCREENING BACTERIA CAPABLE OF DEGRADING ETHYLENE OXIDE

(71) Applicants: Chio Kang Medical, Inc., Palo Alto, CA (US); QIAOKANG BIOTECH (GUANGDONG) CO., LTD., Guangzhou (CN)

(72) Inventors: Jianlong Xue, Guangzhou (CN); Dongxin Hou, Guangzhou (CN); Xin Yin, Guangzhou (CN); Lijuan Jiang, Guangzhou (CN); Xuzhong Liao, Guangzhou (CN); Guqun Ren, Guangzhou (CN); Yecheng He, Guangzhou (CN); Ziping Zhu, Guangzhou (CN); Jiali Lin, Guangzhou (CN); Lixiong Feng, Guangzhou (CN)

(73) Assignees: CHIO KANG MEDICAL, INC., Palo Alto, CA (US); QIAOKANG BIOTECH (GUANGDONG) CO., LTD., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/012,769

(22) Filed: Sep. 4, 2020

Related U.S. Application Data

(63) Continuation-in-part of application No. PCT/CN2020/101143, filed on Jul. 9, 2020.

(30) Foreign Application Priority Data

Jan. 20, 2020 (CN) .......................... 202010064633.4

(51) Int. Cl.
  *C12N 1/20* (2006.01)
  *C12Q 1/04* (2006.01)
  *C12R 1/01* (2006.01)

(52) U.S. Cl.
  CPC .............. *C12N 1/20* (2013.01); *C12Q 1/045* (2013.01); *C12N 2500/05* (2013.01); *C12N 2500/12* (2013.01); *C12N 2500/16* (2013.01); *C12N 2500/30* (2013.01); *C12N 2500/34* (2013.01);
  (Continued)

(58) Field of Classification Search
  CPC ........ A01N 25/12; A01N 43/16; A01N 25/04; A01N 65/40; A23V 2002/00; A23V 2200/10; A23V 2200/254; A23V 2250/511; A23L 29/275; A23L 2/44; A23L 2/52; A23L 33/10; A23L 3/3526; A23L 3/3544; A61K 9/1652; A61K 9/5036; A61K 9/5161; A61K 2039/505; B32B 5/16; C08B 37/003; C08L 5/08; C12G 1/02; C12G 2200/21; C12H 1/14; C12N 1/14; C12N 1/20; C12N 15/8218; C12N 1/02; C12N 1/12; C12N 1/16; C12N 1/36; C12Q 1/689; G01N 2333/335; Y10T 428/2982; A61P 35/00; B01D 2257/708; B01D 53/52; B01D 53/58; B01D 53/84; B09C 1/105; B22F 1/0003; B22F 2009/245; B22F 2301/10; B22F 2301/255; B22F 2301/35; B22F 2304/10; B22F 9/24; C02F 1/44; C02F 1/66; C02F 2103/36; C02F 2305/06; C02F 3/325; C02F 3/34; C02F 9/00; C05F 5/008; C07K 14/415; C07K 16/16; C07K 16/244; C07K 2317/24; C07K 2317/33; C07K 2317/565; C07K 2317/76; C07K 2317/92; C12R 1/07; C12R 1/125; C12R 1/225; C21B 15/00; C22B 11/046; C22B 15/0065; C22B 15/0071; C22B 1/005; C22B 3/08; C22B 3/18; Y02P 10/20; Y02P 10/234
  See application file for complete search history.

(56) References Cited

U.S. PATENT DOCUMENTS

| 1,954,056 | A | 4/1934 | Miller |
| 2,586,670 | A | 2/1952 | Lambertsen |
| 2,817,689 | A | 12/1957 | White |

(Continued)

FOREIGN PATENT DOCUMENTS

| CN | 1223166 A | 7/1999 |
| CN | 1397474 A | 2/2003 |

(Continued)

OTHER PUBLICATIONS

DERWNT-ACC-No. 2017-83105H, Document ID: CN107400637 "New Bacillus coagulans . . . and method for screening . . . ", see abstract only, Nov. 28, 2017. (Year: 2017).*

(Continued)

*Primary Examiner* — Deborah K Ware
(74) *Attorney, Agent, or Firm* — Adsero IP

(57) ABSTRACT

The present disclosure discloses a method for screening bacteria capable of tolerating and degrading ethylene oxide, comprising: preliminary screening, purification, ethylene oxide tolerance acclimatization, and ethylene oxide degradation acclimatization. The methods for screening and acclimatization provided by the present application is simple to operate, and the ability of the acclimatized strains to degrade ethylene oxide is significantly improved. Therefore, a series of ethylene oxide-degrading strains capable of tolerating and degrading ethylene oxide may be obtained, which have excellent treatment performance and is safe, environmentally friendly, and is of great significance for decontamination treatment of ethylene oxide.

11 Claims, 1 Drawing Sheet

Specification includes a Sequence Listing.

(52) U.S. Cl.
CPC ...... *C12N 2500/74* (2013.01); *C12N 2500/84* (2013.01); *C12R 1/01* (2013.01)

(56) References Cited

U.S. PATENT DOCUMENTS

| | | | |
|---|---|---|---|
| 3,022,054 | A | 2/1962 | Kotzebue |
| 3,598,543 | A | 6/1969 | Crosby et al. |
| 3,572,391 | A | 3/1971 | Hirsch et al. |
| 3,844,739 | A | 10/1974 | Alfrey, Jr. |
| 3,961,920 | A | 6/1976 | Gilbert |
| 3,997,633 | A | 12/1976 | Leva et al. |
| 4,112,054 | A | 9/1978 | Feingold et al. |
| 4,119,539 | A | 10/1978 | Ettel et al. |
| 4,134,425 | A | 1/1979 | Gussefeld et al. |
| 4,243,636 | A | 1/1981 | Shiraki et al. |
| 4,274,954 | A | 6/1981 | Blair |
| 4,301,113 | A | 11/1981 | Alguire et al. |
| 4,517,167 | A | 5/1985 | Popescu et al. |
| 4,549,363 | A | 10/1985 | Buonicore |
| 4,831,196 | A | 5/1989 | Buonicore et al. |
| 5,084,075 | A | 1/1992 | Sircar |
| 5,204,075 | A | 4/1993 | Jain et al. |
| 5,270,000 | A | 12/1993 | Goldner et al. |
| 5,283,035 | A | 2/1994 | Karthaus et al. |
| 5,290,345 | A | 3/1994 | Osendorf et al. |
| 5,511,409 | A | 4/1996 | Knaebel |
| 5,522,808 | A | 6/1996 | Skalla |
| 5,607,652 | A | 3/1997 | Hellmuth et al. |
| 5,641,455 | A | 6/1997 | Rosenlund et al. |
| 5,702,669 | A | 12/1997 | Green |
| 5,741,470 | A | 4/1998 | Wenzler |
| 5,755,857 | A | 5/1998 | Acharya et al. |
| 5,779,773 | A | 7/1998 | Cam et al. |
| 5,883,199 | A | 3/1999 | McCarthy |
| 5,964,927 | A | 10/1999 | Graham et al. |
| 6,156,101 | A | 12/2000 | Naheiri |
| 6,684,648 | B2 | 2/2004 | Faqih |
| 6,743,402 | B2 | 6/2004 | Shimakawa |
| 7,625,535 | B2 | 12/2009 | Yamaguchi |
| 8,110,156 | B2 | 2/2012 | Ricciardi et al. |
| 8,431,085 | B2 | 4/2013 | Froderberg et al. |
| 9,616,143 | B2 | 4/2017 | Snyder et al. |
| 10,987,443 | B1 | 4/2021 | Hu et al. |
| 2001/0033838 | A1 | 10/2001 | Farmer |
| 2002/0046569 | A1 | 4/2002 | Faqih |
| 2002/0197194 | A1 | 12/2002 | Machado et al. |
| 2004/0229340 | A1 | 11/2004 | Kawai |
| 2006/0236860 | A1 | 10/2006 | Sumida et al. |
| 2006/0249027 | A1 | 11/2006 | Adolphsen et al. |
| 2007/0209383 | A1 | 9/2007 | Hutton |
| 2008/0078289 | A1 | 4/2008 | Sergi et al. |
| 2008/0080999 | A1 | 4/2008 | Bondar |
| 2008/0289591 | A1 | 11/2008 | Tessier et al. |
| 2010/0196194 | A1 | 8/2010 | Voeten et al. |
| 2010/0291169 | A1 | 11/2010 | Toreki et al. |
| 2011/0265644 | A1 | 11/2011 | Swami et al. |
| 2012/0031268 | A1 | 2/2012 | Yaghi et al. |
| 2012/0298207 | A1 | 11/2012 | Woelk et al. |
| 2014/0119989 | A1 | 5/2014 | Hayashi |
| 2014/0251130 | A1 | 9/2014 | Sprinkle et al. |
| 2014/0290162 | A1 | 10/2014 | Tanimoto |
| 2016/0010883 | A1 | 1/2016 | Jomitz et al. |
| 2016/0130489 | A1 | 5/2016 | Gilmour |
| 2017/0056813 | A1 | 3/2017 | McMahon et al. |
| 2019/0076776 | A1 | 3/2019 | Mahecha-Botero et al. |
| 2019/0151791 | A1 | 5/2019 | Awadh et al. |
| 2019/0175971 | A1 | 6/2019 | Moore et al. |
| 2020/0148655 | A1 | 5/2020 | Duff et al. |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103667014 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103801190 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 104946557 A | 9/2015 |
| CN | 105132060 A | 12/2015 |
| CN | 105327665 A | 2/2016 |
| CN | 105664822 A | 2/2016 |
| CN | 105462903 A | 4/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 106754585 | 5/2017 |
| CN | 107058179 A | 8/2017 |
| CN | 206443946 U | 8/2017 |
| CN | 206535551 U | 10/2017 |
| CN | 107460146 A | 12/2017 |
| CN | 206853397 U | 1/2018 |
| CN | 107677016 A | 2/2018 |
| CN | 207169397 U | 4/2018 |
| CN | 207187436 U | 4/2018 |
| CN | 107988095 A | 5/2018 |
| CN | 207356290 U | 5/2018 |
| CN | 207745676 U | 8/2018 |
| CN | 207913454 U | 9/2018 |
| CN | 108607511 A | 10/2018 |
| CN | 208047841 U | 11/2018 |
| CN | 208218734 U | 12/2018 |
| CN | 109294942 A | 2/2019 |
| CN | 109382064 A | 2/2019 |
| CN | 208448985 U | 2/2019 |
| CN | 208893903 U | 5/2019 |
| CN | 110106086 A | 8/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| CN | 111117931 A | 5/2020 |
| CN | 111117932 A | 5/2020 |
| CN | 111154684 A | 5/2020 |
| CN | 111154687 A | 5/2020 |
| DE | 4236622 C1 | 3/1994 |
| EP | 0130319 A2 | 1/1985 |
| EP | 0350677 A1 | 1/1990 |
| EP | 1238718 A1 | 9/2002 |
| EP | 1302478 A1 | 4/2003 |
| EP | 2883598 A1 | 6/2015 |
| GB | 1472091 A | 4/1977 |
| JP | 2008114210 A | 5/2008 |

(56) References Cited

FOREIGN PATENT DOCUMENTS

| | | |
|---|---|---|
| JP | 2010259648 A | 11/2010 |
| JP | 2013172790 A | 10/2016 |
| JP | 2016221497 A | 12/2016 |
| WO | WO 2006115199 A1 | 11/2006 |
| WO | WO2011002277 A1 | 1/2011 |
| WO | WO 2012013197 A2 | 2/2012 |
| WO | WO-2019-136504 A1 | 7/2019 |
| WO | WO 2019236249 A1 | 12/2019 |

OTHER PUBLICATIONS

U.S. Appl. No. 17/012,797, TrackOne Bypass CON Application, filed Sep. 4, 2020, 79 pages.
U.S. Appl. No. 17/012,810, TrackOne Bypass CON Application, filed Sep. 4, 2020, 73 pages.
U.S. Appl. No. 17/012,828, TrackOne Bypass CON Application, filed Sep. 4, 2020, 86 pages.
U.S. Appl. No. 17/012,843, TrackOne Bypass CON Application, filed Sep. 4, 2020, 67 pages.
CN 103667014-A The relevance of the CN 103667014-A reference is disclosed in the English language abstract submitted herewith.
CN 103800926-A The relevance of the CN 103800926-A reference is disclosed in the English language abstract submitted herewith.
CN 103801190-A The relevance of the CN 103801190-A reference is disclosed in the English language abstract submitted herewith.
CN 104946557-A The relevance of the CN 104946557-A reference is disclosed in the English language abstract submitted herewith.
CN 105462903-A The relevance of the CN 105462903-A reference is disclosed in the English language abstract submitted herewith.
CN 106582126-A The relevance of the CN 106582126-A reference is disclosed in the English language abstract submitted herewith.
CN 107058179-A The relevance of the CN 107058179-A reference is disclosed in the English language abstract submitted herewith.
CN 107460146-A The relevance of the CN 107460146-A reference is disclosed in the English language abstract submitted herewith.
CN 107988095-A The relevance of the CN 107988095-A reference is disclosed in the English language abstract submitted herewith.
CN 109294942-A The relevance of the CN 109294942-A reference is disclosed in the English language abstract submitted herewith.
CN 210088451-U The relevance of the CN 210088451-U is disclosed in the English language abstract submitted herewith.
CN 111117931-A The relevance of the CN 111117931-A reference is disclosed in the English language abstract submitted herewith.
CN 111117932-A The relevance of the CN 111117932-A reference is disclosed in the English language abstract submitted herewith.
CN 111154687-A The relevance of the CN 111154687-A reference is disclosed in the English language abstract submitted herewith.
CN 110106086-A The relevance of the CN 110106086-A reference is disclosed in the English language abstract submitted herewith.
CN 111154684-A The relevance of the CN 111154684-A reference is disclosed in the English language abstract submitted herewith.
CN 103706233-A The relevance of the CN 103706233-A reference is disclosed in the English language abstract submitted herewith.
CN 110145747-A The relevance of the CN 110145747-A reference is disclosed in the English language abstract submitted herewith.
CN 103394278-A The relevance of the CN 103394278-A reference is disclosed in the English language abstract submitted herewith.
CN 203507806-U The relevance of the CN 203507806-U reference is disclosed in the English language abstract submitted herewith.
CN 203750389-U The relevance of the CN 203750389-U reference is disclosed in the English language abstract submitted herewith.
CN 203750388-U The relevance of the CN 203750388-U reference is disclosed in the English language abstract submitted herewith.
CN 203749877-U The relevance of the CN 203749877-U reference is disclosed in the English language abstract submitted herewith.
CN 103657383-A The relevance of the CN 103657383-A reference is disclosed in the English language abstract submitted herewith.
CN 108607511-A The relevance of the CN 108607511-A reference is disclosed in the English language abstract submitted herewith.
CN 208448985-U The relevance of the CN 208448985-U reference is disclosed in the English language abstract submitted herewith.
CN 207169397-U The relevance of the CN 207169397-U reference is disclosed in the English language abstract submitted herewith.
EP 0350677-A1 The relevance of the EP 0350677-A1 reference is disclosed in the English language abstract submitted herewith.
EP 1238718-A1 The relevance of the EP 1238718-A1 reference is disclosed in the English language abstract submitted herewith.
JP 2008114210-A The relevance of the JP 2008114210-A reference is disclosed in the English language abstract submitted herewith.
JP 2016221497-A The relevance of the JP 2016221497-A reference is disclosed in the English language abstract submitted herewith.
WO 2006115199-A1 The relevance of the WO 2006115199-A1 reference is disclosed in the English language abstract submitted herewith.
CN 105664822-A The relevance of the CN 105664822-A reference is disclosed in the English language abstract submitted herewith.
CN 106475021-A The relevance of the CN 106475021-A reference is disclosed in the English language abstract submitted herewith.
CN 204447972-U The relevance of the CN CN 204447972-U reference is disclosed in the English language abstract submitted herewith.
CN 104014227-A The relevance of the CN 104014227-A reference is disclosed in the English language abstract submitted herewith.
CN 104275085-A The relevance of the CN 104275085-A reference is disclosed in the English language abstract submitted herewith.
CN 110302634-A The relevance of the CN 110302634-A reference is disclosed in the English language abstract submitted herewith.
CN 110833754-A The relevance of the CN 110833754-A reference is disclosed in the English language abstract submitted herewith.
CN 110404485-A The relevance of the CN 110404485-A reference is disclosed in the English language abstract submitted herewith.
CN 202933710-U The relevance of the CN 202933710-U reference is disclosed in the English language abstract submitted herewith.
CN 102219642-A The relevance of the CN 102219642-A reference is disclosed in the English language abstract submitted herewith.
CN 206535551-U The relevance of the CN 206535551-U reference is disclosed in the English language abstract submitted herewith.
CN 105327665-A the relevance of the CN 105327665-A reference is disclosed in the English language abstract submitted herewith.
CN 209662917-U The relevance of the CN 209662917-U reference is disclosed in the English language abstract submitted herewith.
CN 206853397-U The relevance of the CN 206853397-U reference is disclosed in the English language abstract submitted herewith.
CN 208893903-U The relevance of the CN 208893903-U reference is disclosed in the English language abstract submitted herewith.
CN 210021633-U The relevance of the CN 210021633-U reference is disclosed in the English language abstract submitted herewith.
CN 101224381-A The relevance of the CN 101224381-A reference is disclosed in the English language abstract submitted herewith.
CN 207913454-U The relevance of the CN 207913454-U reference is disclosed in the English language abstract submitted herewith.
CN 202802975-U The relevance of the CN 202802975-U reference is disclosed in the English language abstract submitted herewith.
CN 102921570-A The relevance of the CN 102921570-A reference is disclosed in the English language abstract submitted herewith.
CN 109382064-A The relevance of the CN 109382064-A reference is disclosed in the English language abstract submitted herewith.
CN 107677016-A The relevance of the CN 107677016-A reference is disclosed in the English language abstract submitted herewith.
CN 205300112-U The relevance of the CN 205300112-U reference is disclosed in the English language abstract submitted herewith.
CN 207745676-U The relevance of the CN 207745676-U reference is disclosed in the English language abstract submitted herewith.
CN 101549241-A The relevance of the CN 101549241-A reference is disclosed in the English language abstract submitted herewith.
CN 102173384-A The relevance of the CN 102173384-A reference is disclosed in the English language abstract submitted herewith.
CN 201632182-U The relevance of the CN 201632182-U reference is disclosed in the English language abstract submitted herewith.
CN 1223166-A The relevance of the CN 1223166-A reference is disclosed in the English language abstract submitted herewith.

(56) References Cited

OTHER PUBLICATIONS

CN 207187436-U The relevance of the CN 207187436-U reference is disclosed in the English language abstract submitted herewith.
CN 105132060-A The relevance of the CN 105132060-A reference is disclosed in the English language abstract submitted herewith.
CN 101773762-A The relevance of the CN 101773762-A reference is disclosed in the English language abstract submitted herewith.
CN 208218734-U The relevance of the CN 208218734-U reference is disclosed in the English language abstract submitted herewith.
CN 104815535-A The relevance of the CN 104815535-A reference is disclosed in the English language abstract submitted herewith.
CN 203564952-U The relevance of the CN 203564952-U reference is disclosed in the English language abstract submitted herewith.
DE 4236622-C1 The relevance of the DE 4236622-C1 reference is disclosed in the English language abstract submitted herewith.
Bao, et al., (2010) Food Control, 21:695-701, "Screening of potential probiotic properties of Lactobacillus fermentum isolated from traditional dairy products".
Brown, et al., (1997) J. Ag and Food Chem. 3(45): 955-961, "Degradation of Thifensulfuron Methyl in Soil: Role of Microbial Carboxyesterase Activity".
Danko, et al., (2008) Proc. Biochem. 43:517-521, "Involvement of carbon dioxide in the aerobic biodegradation of ethylene oxide, ethene, and vinyl chloride".
Fei, et al. (2006) Annals Micro. 3(56):201-205, "Identification of *Enterococcus* sp. from midgut of silkworm based on biochemical and 16S rDNA sequencing analysis".
International Search Report and Written Opinion dated Oct. 28, 2020 in PCT/CN2020/101143, 10 pages.
International Search Report and Written Opinion dated Oct. 21, 2020 in PCT/CN2020/101141, 12 pages.
International Search Report and Written Opinion dated Oct. 27, 2020 in PCT/CN2020/101138, 11 pages.
International Search Report and Written Opinion dated Oct. 28, 2020 in PCT/CN2020/101144, 10 pages.
International Search Report and Written Opinion dated Oct. 28, 2020 in PCT/CN2020/101139, 11 pages.
International Search Report and Written Opinion dated Dec. 16, 2020 in PCT/CN2020/101142, 11 pages.
International Search Report and Written Opinion, in PCT/CN2020/101140 dated Dec. 21, 2020, 11 pages.
International Search Report and Written Opinion, in PCT/CN2020/100143 dated Dec. 21, 2020, 9 pages.
International Search Report and Written Opinion, in PCT/CN2020/100125 dated Dec. 23, 2020, 9 pages.
International Search Report and Written Opinion, in. PCT/CN2020/100115 dated Dec. 16, 2020, 11 pages.
International Search Report and Written Opinion, in. PCT/CN2020/100119 dated Dec. 17, 2020, 9 pages.
International Search Report and Written Opinion, in PCT/CN2020/100144 dated Dec. 18, 2020, 10 pages.
Kahm et al., 2018 "Lyapunov exponents with Model Predictive Control for exothermic batch reactors" IFAC—PapersOnline, 51, 417-422.
Khatiwala, et al. (2008) J. Polym. Environ. 16:61-67, "Biodegradation of poly($\varepsilon$-caprolactone)(PCL) film by alcaligenes faecalis".
Liao, et al., (2001) Environ. Tech. 22:165-173, "Decomposition of ethylene oxide in the RF plasma environment".
Perez-Cano, et al., (2010) Immunobiology 215:996-1004, "In vitro immunomodulatory activity of Lactobacillus fermentum CECT5716 and Lactobacillus salivarius CECT5713: two probiotic strains isolated from human breast milk".
Poelarends, et al., (1999) J. Bact. 7(181):2050-2058, "Degradation of 1, 2-Dibromoethane by *Mycobacterium* sp. Strain GP1".
Shin, et al., (2016) Anaerobe 39:14-18, "*Clostridium kogasensis* sp. nov., a novel member of the genus *Clostridium*, isolated from soil under a corroded gas pipeline".
Sutton, et al. (2018) F1000 Research 7:1-26, "*Enterobacter hormaechei* subsp. *Hoffmannii* subsp. nov., *Enterobacter hormaechei* subsp. xiangfangensis comb. nov., *Enterobacter roggenkampii* sp. nov., and Enterobacter muelleri is a later heterotypic synonym of Enterobacter asburiae based on computational analysis of sequenced Enterobacter genomes".
Taylor, et al., (2010) Appl. Micro. Biotech. 87:2293-2302, "Extending the alkene substrate range of vinyl chloride utilizing *Nocardioides* sp. strain JS614 with ethene oxide".
U.S. Appl. No. 17/012,857, TrackOne Bypass CON Application filed Sep. 4, 2020, 148 pages.
U.S. Appl. No. 17/002,500, TrackOne Bypass CON Application filed Aug. 25, 2020, 61 pages.
U.S. Appl. No. 17/002,523, TrackOne Bypass CON Application filed Aug. 25, 2020, 72 pages.
U.S. Appl. No. 17/002,529, TrackOne Bypass CON Application filed Aug. 25, 2020, 64 pages.
U.S. Appl. No. 17/002,540, TrackOne Bypass CON Application filed Aug. 25, 2020, 89 pages.
U.S. Appl. No. 17/004,730, TrackOne Bypass CON Application filed Aug. 27, 2020, 77 pages.
U.S. Appl. No. 17/012,864, TrackOne Bypass CON Application filed Sep. 4, 2020, 78 pages.
U.S. Appl. No. 17/004,903, TrackOne Bypass CON Application filed Aug. 27, 2020, 67 pages.
U.S. Appl. No. 17/004,930, TrackOne Bypass CON Application filed Aug. 27, 2020, 80 pages.
U.S. Appl. No. 17/004,971, TrackOne Bypass CON Application filed Aug. 27, 2020, 75 pages.
Yin, et al., (2016) Int. J. Hydrogen Energy, 22793-22801, "Characterization and hydrogen production performance of a novel strain *Enterococcus faecium* INET2 isolated from gamma irradiated sludge".
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.

\* cited by examiner

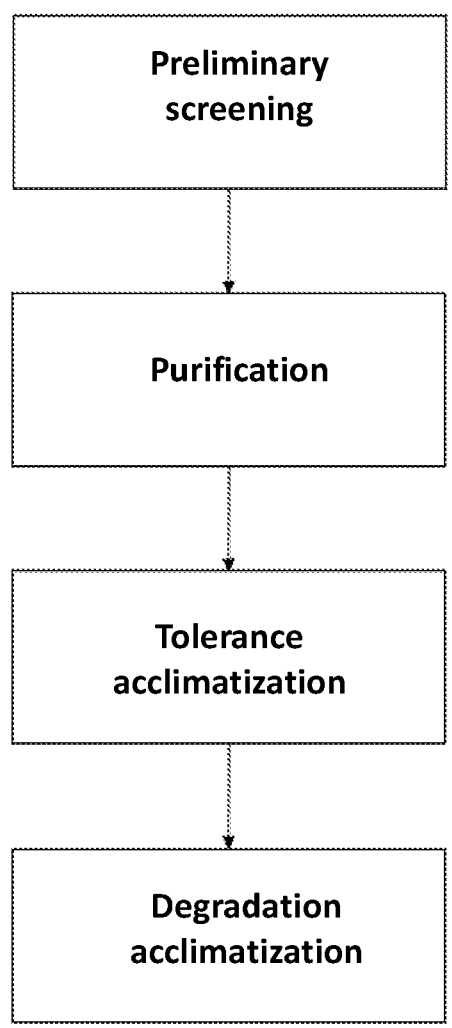

```
                        SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2
ggttaccttg ttacgactt                                               19

<210> SEQ ID NO 3
<211> LENGTH: 1432
<212> TYPE: DNA
<213> ORGANISM: Alcaligenes faecalis

<400> SEQUENCE: 3
gctttaacac atgcaagtcg aacggcagca cgcagagagc ttgctctctt ggtggcgagt    60
```

-continued

```
ggcggacggg tgagtaatat atcggaacgt gcccagtagc ggggggataac tactcgaaag    120
agtggctaat accgcatacg ccctacgggg gaaaggggggg gatcgcaaga cctctcacta    180
ttggagcggc cgatatcgga ttagctagtt ggtggggtaa aggctcacca aggcaacgat    240
ccgtagctgg tttgagagga cgaccagcca cactgggact gagacacggc ccagactcct    300
acgggaggca gcagtgggga attttggaca atgggggaaa ccctgatcca gccatcccgc    360
gtgtatgatg aaggccttcg ggttgtaaag tactttggc agagaagaaa aggcatcccc    420
taatacggga tgctgctgac ggtatctgca gaataagcac cggctaacta cgtgccagca    480
gccgcggtaa tacgtagggt gcaagcgtta atcggaatta ctgggcgtaa agcgtgtgta    540
ggcggttcgg aaagaaagat gtgaaatccc agggctcaac cttggaactg cattttaac     600
tgccgagcta gagtatgtca gaggggggta gaattccacg tgtagcagtg aaatgcgtag    660
atatgtggag gaataccgat ggcgaaggca gccccctggg ataatactga cgctcagaca    720
cgaaagcgtg gggagcaaac aggattagat accctggtag tccacgccct aaacgatgtc    780
aactagctgt tggggccgtt aggccttagt agcgcagcta acgcgtgaag ttgaccgcct    840
ggggagtacg gtcgcaagat taaaactcaa aggaattgac ggggacccgc acaagcggtg    900
gatgatgtgg attaattcga tgcaacgcga aaaaccttac ctaccttga catgtctgga    960
aagccgaaga gatttggcag tgctcgcaag agaaccggaa cacaggtgct gcatggctgt   1020
cgtcagctcg tgtcgtgaga tgttgggtta agtcccgcaa cgagcgcaac ccttgtcatt   1080
agttgctacg caagagcact ctaatgagac tgccggtgac aaaccggagg aaggtgggga   1140
tgacgtcaag tcctcatggc ccttatgggt agggcttcac acgtcataca atggtcggga   1200
cagagggtcg ccaacccgcg agggggagcc aatctcagaa acccgatcgt agtccggatc   1260
gcagtctgca actcgactgc gtgaagtcgg aatcgctagt aatcgcggat cagaatgtcg   1320
cggtgaatac gttcccgggt cttgtacaca ccgcccgtca ccatgggga gtgggtttca   1380
ccagaagtag gtagcctaac cgcaaggagg gcgctaccac ggtgatgatg tc           1432
```

<210> SEQ ID NO 4
<211> LENGTH: 1412
<212> TYPE: DNA
<213> ORGANISM: Acetobacter peroxydans

<400> SEQUENCE: 4

```
agagtttgat catggctcag agcgaacgct ggcggcatgc ttaacacatg caagtcgcac     60
gaaggtttcg gccttagtgg cggacgggtg agtaacgcgt aggaatctat ccatgggtgg    120
gggataacac tgggaaactg gtgctaatac cgcatgacac ctgagggtca aaggcgcaag    180
tcgcctgtgg aggagcctgc gttcgattag ctagttggtg gggtaaaggc ctaccaaggc    240
gatgatcgat agctggtttg agaggatgat cagccacact gggactgaga cacggcccag    300
actcctacgg gaggcagcag tggggaatat tggacaatgg gggcaaccct gatccagcaa    360
tgccgcgtgt gtgaagaagg tcttcggatt gtaaagcact ttcgacgggg acgatgatga    420
cggtacccgt agaagaagcc ccggctaact tcgtgccagc agccgcggta atacgaaggg    480
ggctagcgtt gctcggaatg actgggcgta aaggcgtgt aggcggtttt gacagtcaga    540
tgtgaaatcc ccgggcttaa cctgggagct gcatttgaga cgttaagact agagtgtgag    600
agagggttgt ggaattccca gtgtagaggt gaaattcgta gatattggga agaacaccgg    660
tggcgaaggc ggcaacctgg ctcattactg acgctgaggc gcgaaagcgt ggggagcaaa    720
caggattaga taccctggta gtccacgctg taaacgatgt gtgctagatg ttgggtaact    780
```

| | |
|---|---|
| tagttactca gtgtcgcagt taacgcgtta agcacaccgc ctggggagta cggccgcaag | 840 |
| gttgaaactc aaaggaattg acggggggccc gcacaagcgg tggagcatgt ggtttaattc | 900 |
| gaagcaacgc gcagaacctt accagggctt gaatgtggag gctgtaggca gagatgtcta | 960 |
| tttcttcgga cctccaacac aggtgctgca tggctgtcgt cagctcgtgt cgtgagatgt | 1020 |
| tgggttaagt cccgcaacga gcgcaacccc tatctttagt tgccagcatg tttgggtggg | 1080 |
| cactctagag agactgccgg tgacaagccg aggaaggtg gggatgacgt caagtcctca | 1140 |
| tggcccttat gtcctgggct acacacgtgc tacaatggcg gtgacagtgg gaagctatgt | 1200 |
| ggtgacacag tgctgatctc taaaagccgt ctcagttcgg attgcactct gcaactcgag | 1260 |
| tgcatgaagg tggaatcgct agtaatcgcg gatcagcatg ccgcggtgaa tacgttcccg | 1320 |
| ggccttgtac acaccgcccg tcacaccatg ggagtggttt gaccttaagc cggtgagcga | 1380 |
| accgcaagga cgcagccgac cacgtcgtcg ct | 1412 |

<210> SEQ ID NO 5
<211> LENGTH: 1453
<212> TYPE: DNA
<213> ORGANISM: Lactobacillus fermentum

<400> SEQUENCE: 5

| | |
|---|---|
| gcggctggct cctaaaaggt taccccaccg actttgggtg ttacaaactc tcatggtgtg | 60 |
| acgggcggtg tgtacaaggc ccgggaacgt attcaccgcg gcatgctgat ccgcgattac | 120 |
| tagcgattcc gacttcgtgc aggcgagttg cagcctgcag tccgaactga aacggtttt | 180 |
| aagagatttg cttgccctcg cgagttcgcg actcgttgta ccgtccattg tagcacgtgt | 240 |
| gtagcccagg tcataagggg catgatgatc tgacgtcgtc cccaccttcc tccggtttgt | 300 |
| caccggcagt ctcactagag tgcccaactt aatgctggca actagtaaca agggttgcgc | 360 |
| tcgttgcggg acttaaccca acatctcacg cacgagctg acgacgacca tgcaccacct | 420 |
| gtcattgcgt tcccgaagga aacgccctat ctctagggtt ggcgcaagat gtcaagacct | 480 |
| ggtaaggttc ttcgcgtagc ttcgaattaa accacatgct ccaccgcttg tgcgggcccc | 540 |
| cgtcaattcc tttgagtttc aaccttgcgg tcgtactccc caggcggagt gcttaatgcg | 600 |
| ttagctccgg cactgaaggg cggaaaccct ccaacaccta gcactcatcg tttacggcat | 660 |
| ggactaccag ggtatctaat cctgttcgct acccatgctt tcgagtctca gcgtcagttg | 720 |
| cagaccaggt agccgccttc gccactggtg ttcttccata tatctacgca ttccaccgct | 780 |
| acacatggag ttccactacc ctcttctgca ctcaagttat ccagtttccg atgcacttct | 840 |
| ccggttaagc cgaaggcttt cacatcagac ttagaaaacc gcctgcactc tctttacgcc | 900 |
| caataaatcc ggataacgct tgccacctac gtattaccgc ggctgctggc acgtagttag | 960 |
| ccgtgacttt ctggttaaat accgtcaacg tatgaacagt tactctcata cgtgttcttc | 1020 |
| tttaacaaca gagctttacg agccgaaacc cttcttcact cacgcggtgt tgctccatca | 1080 |
| ggcttgcgcc cattgtggaa gattccctac tgctgcctcc cgtaggagta tgggccgtgt | 1140 |
| ctcagtccca ttgtggccga tcagtctctc aactcggcta tgcatcatcg ccttggtagg | 1200 |
| ccgttacccc accaacaagc taatgcaccg caggtccatc cagaagtgat agcgagaagc | 1260 |
| catcttttaa gcgttgttca tgcgaacaac gctgttatgc ggtattagca tctgtttcca | 1320 |
| aatgttgtcc cccgcttctg ggcaggttac ctacgtgtta ctcacccgtc cgccactcgt | 1380 |
| tggcgaccaa aatcaatcag gtgcaagcac catcaatcaa ttgggccaac gcgttcgact | 1440 | gcattattag gca                                                              1453

<210> SEQ ID NO 6
<211> LENGTH: 1439
<212> TYPE: DNA
<213> ORGANISM: Bacillus subtilis

<400> SEQUENCE: 6

| | | | | | |
|---|---|---|---|---|---|
| ctatacatgc | aagtcgagcg | gacagatggg | agcttgctcc | ctgatgttag | cggcggacgg | 60 |
| gtgagtaaca | cgtgggtaac | ctgcctgtaa | gactgggata | actccgggaa | accggggcta | 120 |
| ataccggatg | gttgtttgaa | ccgcatggtt | cagacataaa | aggtggcttc | ggctaccact | 180 |
| tacagatgga | cccgcggcgc | attagctagt | tggtgaggta | acggctcacc | aaggcgacga | 240 |
| tgcgtagccg | acctgagagg | gtgatcggcc | acactgggac | tgagacacgg | cccagactcc | 300 |
| tacgggaggc | agcagtaggg | aatcttccgc | aatggacgaa | agtctgacgg | agcaacgccg | 360 |
| cgtgagtgat | gaaggttttc | ggatcgtaaa | gctctgttgt | tagggaagaa | caagtgccgt | 420 |
| tcaaataggg | cggcaccttg | acggtaccta | accagaaagc | cacggctaac | tacgtgccag | 480 |
| cagccgcggt | aatacgtagg | tggcaagcgt | tgtccggaat | tattgggcgt | aaagggctcg | 540 |
| caggcggttt | cttaagtctg | atgtgaaagc | ccccggctca | accggggagg | gtcattggaa | 600 |
| actgggaac | ttgagtgcag | aagaggagag | tggaattcca | cgtgtagcgg | tgaaatgcgt | 660 |
| agagatgtgg | aggaacacca | gtggcgaagg | cgactctctg | gtctgtaact | gacgctgagg | 720 |
| agcgaaagcg | tggggagcga | acaggattag | ataccctggt | agtccacgcc | gtaaacgatg | 780 |
| agtgctaagt | gttaggggt | ttccgcccct | tagtgctgca | gctaacgcat | taagcactcc | 840 |
| gcctggggag | tacggtcgca | agactgaaac | tcaaaggaat | tgacggggc | ccgcacaagc | 900 |
| ggtggagcat | gtggtttaat | tcgaagcaac | gcgaagaacc | ttaccaggtc | ttgacatcct | 960 |
| ctgacaatcc | tagagatagg | acgtcccctt | cgggggcaga | gtgacaggtg | gtgcatggtt | 1020 |
| gtcgtcagct | cgtgtcgtga | gatgttgggt | taagtcccgc | aacgagcgca | acccttgatc | 1080 |
| ttagttgcca | gcattcagtt | gggcactcta | aggtgactgc | cggtgacaaa | ccggaggaag | 1140 |
| gtggggatga | cgtcaaatca | tcatgcccct | tatgacctgg | gctacacacg | tgctacaatg | 1200 |
| gcagaacaa | agggcagcga | aaccgcgagg | ttaagccaat | cccacaaatc | tgttctcagt | 1260 |
| tcggatcgca | gtctgcaact | cgactgcgtg | aagctgaat | cgctagtaat | cgcggatcag | 1320 |
| catgccgcgg | tgaatacgtt | cccgggcctt | gtacacaccg | cccgtcacac | cacgagagtt | 1380 |
| tgtaacaccc | gaagtcggtg | aggtaacctt | ttaggagcca | gccgccgaag | gttggacag | 1439 |

<210> SEQ ID NO 7
<211> LENGTH: 1430
<212> TYPE: DNA
<213> ORGANISM: Kurthia gibsonii

<400> SEQUENCE: 7

| | | | | | |
|---|---|---|---|---|---|
| ctatacatgc | agtcgagcga | atgacgagaa | gcttgcttct | ctgatttagc | ggcggacggg | 60 |
| tgagtaacac | gtgggcaacc | tgccctacag | atcgggataa | ctcagggaaa | cctgggctaa | 120 |
| taccggataa | tccttcgaat | cacatgttttt | gaagttgaaa | ggcgcttcgg | cgtcactgta | 180 |
| ggatgggccc | gcggtgcatt | agctagttgg | tggggtaacg | gcctaccaag | gcaacgatgc | 240 |
| atagccgacc | tgagagggtg | atcggccaca | ttgggactga | gacacggccc | aaactcctac | 300 |
| gggaggcag | agtagggaat | cttccacaat | ggacgaaagt | ctgatggagc | aacgccgcgt | 360 |
| gagtgatgaa | ggttttcgga | tcgtaaaact | ctgttgtaag | ggaagaacaa | gtacgttagg | 420 |

```
aaatgaacgt accttgacgg taccttatta gaaagccacg gctaactacg tgccagcagc      480
cgcggtaata cgtaggtggc aagcgttgtc cggatttatt gggcgtaaag cgcgcgcagg      540
tggtttctta agtctgatgt gaaagcccac ggctcaaccg tggagggtca ttggaaactg      600
gggaacttga gtgcagaaga ggatagtgga attccaagtg tagcggtgaa atgcgtagag      660
atttggagga acaccagtgg cgaaggcgac tgtctggtct gtaactgaca ctgaggcgcg      720
aaagcgtggg gagcaaacag gattagatac cctggtagtc cacgccgtaa acgatgagtg      780
ctaagtgtta gggggtttcc gcccctagt gctgcagcta acgcattaag cactccgcct      840
ggggagtacg accgcaaggt tgaaactcaa aggaattgac gggggcccgc acaagcggtg      900
gagcatgtgg tttaattcga agcaacgcga agaaccttac caggtcttga catcccaatg      960
accgtcctag atataggatt tccccttcgg ggacattggt gacaggtggt gcatggttgt     1020
cgtcagctcg tgtcgtgaga tgttgggtta agtcccgcaa cgagcgcaac ccttattctt     1080
agttgccatc atttagttgg gcactctaag gagactgccg gtgacaaacc ggaggaaggt     1140
ggggatgacg tcaaatcatc atgccccttta tgacctgggc tacacacgtg ctacaatgga     1200
cgatacaaag agtcgcaaac tcgcgagggt aagctaatct cataaaatcg ttctcagttc     1260
ggattgtagg ctgcaactcg cctgcatgaa gccggaatcg ctagtaatcg cggatcagca     1320
tgccgcggtg aatacgttcc cgggccttgt acacaccgcc cgtcacacca cgagagtttg     1380
taacacccga gtcggtgggg taaccgtaa ggagccagcc gctaagtgaa                  1430
```

<210> SEQ ID NO 8
<211> LENGTH: 1432
<212> TYPE: DNA
<213> ORGANISM: Clostridium acidisoli

<400> SEQUENCE: 8

```
agagtttgat catggctcag gacgaacgct ggcggcgtgc ttaacacatg caagtcgagc       60
gagaaacctt cgggtttcta gcggcggacg ggtgagtaac acgtgggtaa cctgcctcaa      120
agtgggggat agccttccga aaggaagatt aataccgcat aacattgtag cttcgcatga      180
agcaacaatt aaaggagtaa tccgctttga gatggacccg cggcgcatta gctagttgga      240
gaggtaacgg ctcaccaagg cgacgatgcg tagccgacct gagagggtga tcggccacat      300
tggaactgag acacggtcca gactcctacg ggaggcagca gtggggaata ttgcacaatg      360
ggcgaaagcc tgatgcagca acgccgcgtg agtgatgaag gtcttcggat tgtaaagctc      420
tgtcttttgg gacgataatg acggtaccaa aggaggaagc cacggctaac tacgtgccag      480
cagccgcggt aatacgtagg tggcaagcgt tgtccggaat tactgggcgt aaaggatgtg      540
taggcggata tttaagtgag atgtgaaatc cccgagctca acttgggggc tgcatttcaa      600
actgggtatc tagagtgcag gagaggaaag cggaattcct agtgtagcgg tgaaatgcgt      660
agagattagg aagaacatca gtggcgaagg cggctttctg gactgtaact gacgctgagg      720
catgaaagcg tggggagcaa acaggattag ataccctggt agtccacgcc gtaaacgatg      780
agtactaggt gtaggaggta tcgactcctt ctgtgccgca gttaacacaa taagtactcc      840
gcctgggaag tacggtcgca agattaaaac tcaaaggaat tgacggggc ccgcacaagc      900 agcggagcat gtggtttaat tcgaagcaac gcgaagaacc ttacctagac ttgacatccc      960
ctgaataacg tagagatacg cgaagccctt cggggcaggg agacaggtgg tgcatggttg     1020
tcgtcagctc gtgtcgtgag atgttgggtt aagtcccgca acgagcgcaa cccttatcat     1080
```

| | |
|---|---|
| tagttgctac catttagttg agcactctag tgagactgcc cgggttaacc gggaggaagg | 1140 |
| cggggatgac gtcaaatcat catgcccctt atgtctaggg ctacacacgt gctacaatgg | 1200 |
| tgagaacaac gagatgcaat accgcgaggt ggagcaaaac ttcaaaactc atctcagttc | 1260 |
| ggattgtagg ctgaaactcg cctacatgaa gttggagttg ctagtaatcg cgaatcagaa | 1320 |
| tgtcgcggtg aatacgttcc cgggccttgt acacaccgcc cgtcacacca tgagagctgg | 1380 |
| taacacccga agtccgtgag gtaacctttta ttggggccag cggccgaagg tg | 1432 |

<210> SEQ ID NO 9
<211> LENGTH: 1438
<212> TYPE: DNA
<213> ORGANISM: Enterococcus faecium

<400> SEQUENCE: 9

| | |
|---|---|
| gcggctggct ccaaaaggtt acctcaccga cttcgggtgt tacaaactct cgtggtgtga | 60 |
| cgggcggtgt gtacaaggcc cgggaacgta ttcaccgcgg cgtgctgatc cgcgattact | 120 |
| agcgattccg gcttcatgca ggcgagttgc agcctgcaat ccgaactgag agaagcttta | 180 |
| agagattagc ttagcctcgc gacttcgcaa ctcgttgtac ttcccattgt agcacgtgtg | 240 |
| tagcccaggt cataagggc atgatgattt gacgtcatcc ccaccttcct ccggtttgtc | 300 |
| accggcagtc ttgctagagt gcccaactga atgatggcaa ctaacaataa gggttgcgct | 360 |
| cgttgcggga cttaacccaa catctcacga cacgagctga cgacaaccat gcaccacctg | 420 |
| tcactttgcc cccgaagggg aagctctatc tctagagtgg tcaaaggatg tcaagacctg | 480 |
| gtaaggttct tcgcgttgct tcgaattaaa ccacatgctc caccgcttgt gcgggccccc | 540 |
| gtcaattcct ttgagtttca accttgcggt cgtactcccc aggcggagtg cttaatgcgt | 600 |
| tagctgcagc actgaagggc ggaaaccctc caacacttag cactcatcgt ttacggcgtg | 660 |
| gactaccagg gtatctaatc ctgtttgctc cccacgcttt cgagcctcag cgtcagttac | 720 |
| agaccagaga gccgccttcg ccactggtgt tcctccatat atctacgcat ttcaccgcta | 780 |
| cacatggaat tccactctcc tcttctgcac tcaagtctcc cagtttccaa tgaccctccc | 840 |
| cggttgagcc ggggggcttttc acatcagact taagaaaccg cctgcgctcg ctttacgccc | 900 |
| aataaatccg gacaacgctt gccacctacg tattaccgcg gctgctggca cgtagttagc | 960 |
| cgtggctttc tggttagata ccgtcaaggg atgaacagtt actctcatcc ttgttcttct | 1020 |
| ctaacaacag agttttacga tccgaaaacc ttcttcactc acgcggcgtt gctcggtcag | 1080 |
| actttcgtcc attgccgaag attccctact gctgcctccc gtaggagttt gggccgtgtc | 1140 |
| tcagtcccaa tgtggccgat caccctctca ggtcggctat gcatcgtggc cttggtgagc | 1200 |
| cgttacctca ccaactagct aatgcaccgc gggtccatcc atcagcgaca cccgaaagcg | 1260 |
| cctttcaaat caaaaccatg cggttttgat tgttatacgg tattagcacc tgtttccaag | 1320 |
| tgttatcccc ttctgatggg caggttaccc acgtgttact cacccgttcg ccactcctct | 1380 |
| ttttccggtg gagcaagctc cggtggaaaa agaagcgtgc gacttgcacg tattaggc | 1438 |

<210> SEQ ID NO 10
<211> LENGTH: 1487
<212> TYPE: DNA
<213> ORGANISM: Enterococcus azikeevi

<400> SEQUENCE: 10

| | |
|---|---|
| agagtttgaa tcatggctca ggacgaacgc tggcggcgtg cctaatacat gcaagtcgaa | 60 |
| cgcttctttt tccaccggag cttgctccac cggaaaaaga ggagtggcga acgggtgagt | 120 |

```
aacacgtggg taacctgccc atcagaaggg gataacactt ggaaacaggt gctaataccg       180
tataacaatc gaaaccgcat ggttttgatt gaaaggcgc tttcgggtgt cgctgatgga        240
tggacccgcg gtgcattagc tagttggtga ggtaacggct caccaaggcg acgatgcata       300
gccgacctga gagggtgatc ggccacattg ggactgagac acggcccaaa ctcctacggg       360
aggcagcagt agggaatctt cggcaatgga cgaaagtctg accgagcaac gccgcgtgag       420
tgaagaaggt tttcggatcg taaaactctg ttgttagaga agaacaagga tgagagtaac       480
tgttcatccc ttgacggtat ctaaccagaa agccacggct aactacgtgc cagcagccgc       540
ggtaatacgt aggtggcaag cgttgtccgg atttattggg cgtaaagcga gcgcaggcgg       600
tttcttaagt ctgatgtgaa agcccccggc tcaaccgggg agggtcattg gaaactggga       660
gacttgagtg cagaagagga gagtggaatt ccatgtgtag cggtgaaatg cgtagatata       720
tggaggaaca ccagtggcga aggcggctct ctggtctgta actgacgctg aggctcgaaa       780
gcgtggggag caaacaggat tagataccct ggtagtccac gccgtaaacg atgagtgcta       840
agtgttggag ggtttccgcc cttcagtgct gcagctaacg cattaagcac tccgcctggg       900
gagtacgacc gcaaggttga aactcaaagg aattgacggg ggcccgcaca agcggtggag       960
catgtggttt aattcgaagc aacgcgaaga accttaccag gtcttgacat cctttgacca      1020
ctctagagat agagcttccc cttcggggc aaagtgacag gtggtgcatg gttgtcgtca      1080
gctcgtgtcg tgagatgttg ggttaagtcc cgcaacgagc gcaacccctta ttgttagttg      1140 ccatcattta gttgggcact ctagcaagac tgccggtgac aaaccggagg aaggtgggga      1200
tgacgtcaaa tcatcatgcc ccttatgacc tgggctacac acgtgctaca atgggaagta      1260
caacgagtcg caaagtcgcg aggctaagct aatctcttaa agcttctctc agttcggatt      1320
gtaggctgca actcgcctac atgaagccgg aatcgctagt aatcgcggat cagcacgccg      1380
cggtgaatac gttcccgggc cttgtacaca ccgcccgtca caccacgaga gtttgtaaca      1440
cccgaagtcg gtgaggtaac cttttggagc cagccgccta aggtgat                   1487

<210> SEQ ID NO 11
<211> LENGTH: 1429
<212> TYPE: DNA
<213> ORGANISM: Enterobacter roggenkampii

<400> SEQUENCE: 11
gcagctacac atgcaagtcg agcggcagcg gaagtagctt gctactttgc cggcgagcgg        60
cggacgggtg agtaatgtct gggaaactgc ctgatggagg gggataacta ctggaaacgg       120
tagctaatac cgcataacgt cgcaagacca agagggggga ccttcgggcc tcttgccatc       180
agatgtgccc agatgggatt agctagtagg tggggtaacg gctcacctag gcgacgatcc       240
ctagctggtc tgagaggatg accagccaca ctggaactga gacacggtcc agactcctac       300
gggaggcagc agtggggaat attgcacaat gggcgcaagc ctgatgcagc catgccgcgt       360
gtatgaagaa ggccttcggg ttgtaaagta ctttcagcgg ggaggaaggc gttgaggtta       420
ataacctcag cgattgacgt tacccgcaga agaagcaccg gctaactccg tgccagcagc       480
cgcggtaata cggagggtgc aagcgttaat cggaattact gggcgtaaag cgcacgcagg       540
cggtctgtca agtcggatgt gaaatccccg ggctcaacct gggaactgca ttcgaaactg       600
gcaggctaga gtcttgtaga gggggtaga attccaggtg tagcggtgaa atgcgtagag       660
atctggagga ataccggtgg cgaaggcggc cccctggaca aagactgacg ctcaggtgcg       720
```

```
aaagcgtggg gagcaaacag gattagatac cctggtagtc cacgccgtaa acgatgtcga    780
cttggaggtt gtgcccttga ggcgtggctt ccggagctaa cgcgttaagt cgaccgcctg    840
gggagtacgg ccgcaaggtt aaaactcaaa tgaattgacg ggggcccgca caagcggtgg    900
agcatgtggt ttaattcgat gcaacgcgaa gaaccttacc tactcttgac atccagagaa    960
cttagcagag atgctttggt gccttcggga actctgagac aggtgctgca tggctgtcgt   1020
cagctcgtgt tgtgaaatgt tgggttaagt cccgcaacga gcgcaaccct tatcctttgt   1080
tgccagcggt ccggccggga actcaaagga gactgccagt gataaactgg aggaaggtgg   1140
ggatgacgtc aagtcatcat ggcccttacg agtagggcta cacacgtgct acaatggcgc   1200
atacaaagag aagcgacctc gcgagagcaa gcggacctca taaagtgcgt cgtagtccgg   1260
attggagtct gcaactcgac tccatgaagt cggaatcgct agtaatcgta gatcagaatg   1320
ctacggtgaa tacgttcccg ggccttgtac acaccgcccg tcacaccatg ggagtgggtt   1380
gcaaaagaag taggtagctt aaccttcgggagggcgctac cacttgatt              1429

<210> SEQ ID NO 12
<211> LENGTH: 1401
<212> TYPE: DNA
<213> ORGANISM: Clostridium kogasensis

<400> SEQUENCE: 12
cggcagctac acatgcaagt cgagcgatga atcccttcg gggatggatt agcggcggac     60
gggtgagtaa cacgtgggca acctgcctca agtgggggga tagcctcccg aaagggagat    120
taataccgca taatgttaga tcttcacatg aagaactaat taaggagca atccgctttg    180 agatgggccc gcggcgcatt agctagttgg tgaggtaatg gctcaccaag gcgacgatgc    240
gtagccgacc tgagagggtg atcggccaca ttggaactga gacacggtcc agactcctac    300
gggaggcagc agtggggaat attgcacaat ggggggaaacc ctgatgcagc aacgccgcgt    360
gagtgatgaa ggtcttcgga ttgtaaagct ctgtcttttg gacgataat gacggtacca    420 aaggaggaag ccacggctaa ctacgtgcca gcagccgcgg taatacgtag gtggcgagcg    480
ttgtccggat ttactgggcg taaagggtgc gtaggcggat atttaagtgg gatgtgaaat    540
acccgggctc aacttgggtg ctgcattcca aactggatat ctagagtgcg ggagaggaga    600
gtggaattcc tagtgtagcg gtgaaatgcg tagagattag gaagaacacc agtggcgaag    660
gcgactctct ggaccgtaac tgacgctgag gcacgaaagc gtggggagca acaggatta    720 gataccctgg tagtccacgc cgtaaacgat gaatactagg tgtaggaggt atcgacccct    780
tctgtgccgc agttaacaca ataagtattc cgcctgggga gtacggtcgc aagattaaaa    840
ctcaaaggaa ttgacggggg cccgcacaag cagcggagca tgtggtttaa ttcgaagcaa    900
cgcgaagaac cttacctaga cttgacatac cctgaattac cggtaatgcg gaagcccttc    960 ggggcaggg atacaggtgg tgcatggttg tcgtcagctc gtgtcgtgag atgttaggt   1020 aagtcctgca acgagcgcaa cccctattat tagttgctac cattaagttg agcactctag   1080
taagactgcc tgggttaacc aggaggaagg cgggatgac gtcaaatcat catgcccctt   1140
atgtctaggg ctacacacgt gctacaatgg cggtacaaa aagatgcaaa ctcgcgagag   1200
tgagccaaac tttaaaaccg cccccagttc ggattgtagg ctgaaactcg cctacatgaa   1260
gccggagttg ctagtaatcg cgaatcagca tgtcgcggtg aatacgttcc cgggccttgt   1320
```

```
acacaccgcc cgtcacacca tgagagctgg caacacccga agtccgtgag gtaaccgtaa    1380
ggagccagcg gccgaagtgg g                                              1401
```

METHOD FOR SCREENING BACTERIA CAPABLE OF DEGRADING ETHYLENE OXIDE

CROSS-REFERENCE TO RELATED PATENT APPLICATIONS

This application is a Continuation-in-part of application PCT/CN2020/101143, filed on Jul. 9, 2020, which application claims the benefit of Chinese Patent Application No. 202010064633.4, filed on Jan. 20, 2020, the entire contents of which are incorporated herein by reference in their entirety for all purposes.

TECHNICAL FIELD

The present disclosure relates to biodegradation technology, and more specifically, to a method for screening ethylene oxide-degrading bacteria.

SEQUENCE STATEMENT

Incorporated by reference herein in its entirety is the Sequence Listing entitled "1211_CK01_ST25_PCT" created July 6, size of 19.8 kilobytes.

BACKGROUND

Ethylene oxide (EO) is one of the most important petrochemicals in modern chemical industry. As ethylene oxide has a small molecular weight, high penetrability, and is capable of coupling with biological macromolecules such as DNA and protein, it has an irreplaceable position in the medical sterilization industry. Further, ethylene oxide has a low sterilization cost and enables industrial-grade mass sterilization, and thus is one of the most important low-temperature sterilizers to date.

However, ethylene oxide in use may produce residuals and result in environmental pollution. At present, the following methods are used to treat ethylene oxide: direct high-altitude emission, which pollutes the environment and poses great biological hazards; catalytic combustion, which directly combusts the sterilization waste gas, with safety risks as ethylene oxide is flammable and explosive; and, absorption, which produces glycol by acid catalysis, which can only treat high-concentration ethylene oxide waste gas, and the acid will cause secondary pollution Microbial degradation of pollutants is a common method, but ethylene oxide inhibits microbial growth. Conventional fermenting bacteria cannot tolerate a high concentration of ethylene oxide and the degradation of ethylene oxide is very limited. There have been few studies on microbial degradation of ethylene oxide, and no effective strains that can effectively degrade ethylene oxide or the use thereof have been reported.

SUMMARY

In view of this, the present disclosure provides a method for screening bacteria strains capable of tolerating and degrading ethylene oxide.

In one aspect, the present disclosure provides a method for manufacturing bacteria strains capable of tolerating and degrading ethylene oxide, comprising subjecting a bacteria having a potential for degrading ethylene oxide to ethylene oxide tolerance acclimatization and degradation acclimatization, wherein the ethylene oxide tolerance acclimatization and degradation acclimatization comprises: culturing the bacteria having a potential for degrading ethylene oxide sequentially on ethylene oxide tolerance acclimatization media containing a gradient of increasing concentrations of ethylene oxide; after each culturing, selecting a single colony having a largest radius for further culturing on an ethylene oxide tolerance acclimatization medium containing a next concentration in the gradient of ethylene oxide; and finally selecting a single colony having a largest radius on an ethylene oxide tolerance acclimatization medium containing a highest concentration in the gradient of ethylene oxide, to obtain an ethylene oxide-tolerant bacteria; and, culturing the ethylene oxide-tolerant bacteria sequentially on ethylene oxide degradation acclimatization media containing ethylene oxide and a gradient of decreasing concentrations of carbohydrate carbon source for culturing; after each culturing, selecting a single colony having a largest radius for further culturing on an ethylene oxide degradation acclimatization medium containing a next concentration in the gradient of carbohydrate carbon source; and finally, selecting a single colony having a largest radius on an ethylene oxide degradation acclimatization medium containing a lowest concentration in the gradient of carbohydrate carbon source, to obtain the bacteria capable of tolerating and degrading ethylene oxide.

In another aspect, the present disclosure provides a method for screening bacteria having a potential for degrading ethylene oxide, comprising: collecting a sludge containing ethylene oxide and having microbial activity, treating the sludge to obtain a suspension, providing an enrichment medium, and culturing the suspension in the enrichment medium added with ethylene oxide, to obtain strains having a potential for degrading ethylene oxide; and, culturing the potential strains on a purification medium, and selecting a single colony having a largest radius for further culturing on the enrichment medium with ethylene oxide added, to obtain bacteria having a potential for degrading ethylene oxide.

In another aspect, the present disclosure further provides a method for screening or producing bacteria capable of degrading ethylene oxide, comprising: screening bacteria having a potential for degrading ethylene oxide according to the method in the above-mentioned aspects; and acclimatizing the bacteria having a potential for degrading ethylene oxide in tolerance to and degradation of ethylene oxide according to the method in the above-mentioned aspects.

The screening and acclimatizing method provided in the present application is simple to operate, and the ability of the acclimatized strains to degrade ethylene oxide is significantly improved. Therefore, a series of ethylene oxide-degrading strains capable of tolerating and degrading ethylene oxide may be obtained, which have excellent treatment performance and is safe, environmentally friendly, and is of great significance for decontamination treatment of ethylene oxide.

The application of the methods of the invention resulted in the isolation of several bacterial strains capable of degrading ethylene oxide. Some of these strains include:

*Alcaligenes faecalis* strain EO-05 with the Deposit Number of CGMCC No. 18435;

*Alcaligenes faecalis* strain comprising the 16S rDNA sequence of SEQ ID NO: 3;

*Acetobacter peroxydans* EO-01 strain with Deposit number of CGMCC No. 18431;

*Acetobacter peroxydans* strain comprising the 16S rDNA sequence of SEQ ID NO: 4;

*Lactobacillus fermentum* EO-02 strain with Deposit number of CGMCC No. 18432;

*Lactobacillus fermentum* strain comprising the 16S rDNA sequence of SEQ ID NO: 5;

*Bacillus subtilis* EO-03 strain with Deposit number of CGMCC No. 18433;

*Bacillus subtilis* strain comprising the 16S rDNA sequence of SEQ ID NO: 6;

*Kurthia gibsonii* strain EO-06 with Deposit Number of CGMCC No. 18436;

*Kurthia gibsonii* strain comprising the 16S rDNA sequence of SEQ ID NO: 7;

*Clostridium acidisoli* strain EO-09 with Deposit Number of CGMCC No. 18439;

*Clostridium acidisoli* strain comprising the 16S rDNA sequence of SEQ ID NO: 8;

*Enterococcus faecium* EO-04, with the deposit number CGMCC No. 18434;

*Enterococcus faecium* strain comprising the 16S rDNA sequence of SEQ ID NO: 9;

*Enterococcus azikeevi* EO-07, with the deposit number CGMCC No. 18437;

*Enterococcus azikeevi* strain comprising the 16S rDNA sequence of SEQ ID NO: 10;

*Enterobacter roggenkampii* EO-10, with the deposit number CGMCC No. 18440;

*Enterobacter roggenkampii* strain comprising the 16S rDNA sequence of SEQ ID NO: 11.

*Clostridium kogasensis* strain EO-08 with the Deposit number of CGMCC No. 18438; and

*Clostridium kogasensis* strain comprising the 16S rDNA sequence of SEQ ID NO: 12.

The deposited strains described above and throughout this document were deposited at China General Microbiological Culture Collection Center, with the deposit address being Institute of Microbiology of Chinese Academy of Sciences, NO. 1 West Beichen Road, Beijing 100101, China.

In another aspect of the present disclosure, the degradation rate of ethylene oxide of the resulting strains is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of the strain.

BRIEF DESCRIPTION OF THE DRAWINGS

FIG. 1 shows a flow chart of a method for screening ethylene oxide-degrading bacteria according to one embodiment of the present disclosure.

DETAILED DESCRIPTION OF THE EMBODIMENTS

Examples of the disclosure are described below with more details with reference to the accompanying drawings. It should be understood, however, that the examples are representative and should not be construed as limiting the scope of the present disclosure. Rather, these examples are provided so that this disclosure will be thorough and complete, and will fully convey the scope of the disclosure to those skilled in the art.

Unless otherwise defined, all terms herein, including technical and scientific terms, shall have the same meaning as commonly accepted by a person skilled in the art to which this disclosure belongs. Such terms, as used herein, are for the purpose of describing representative examples of, and without limiting, the present disclosure. The term "and/or" as used herein refers to any and all combinations of one or more items recited.

The chemicals used in the embodiments of the present application are commercially available. The methods not mentioned herein which belong to routine experimental methods will not be described in details.

In one aspect of the present disclosure, there provides a method for screening bacteria having a potential for degrading ethylene oxide, comprising:

preliminary screening: collecting a sludge containing ethylene oxide and having microbial activity, treating the sludge to obtain a suspension, providing an enrichment medium, and culturing the suspension in the enrichment medium added with ethylene oxide, to obtain strains having a potential for degrading ethylene oxide; and, purification: culturing the potential strains on a purification medium, and selecting a single colony having a largest radius for further culturing on the enrichment medium with no ethylene oxide added, to obtain bacteria having a potential for degrading ethylene oxide.

In some embodiments of the above-mentioned aspects, the sludge may for example any one selected from the group consisted of: sludge from a drain outlet of a sewage treatment plant, sludge from a drain outlet of chemical plant, wasteyard sludge, or any mixture thereof.

In some embodiments of the above-mentioned aspects, the treating may comprise adding the sludge into a buffer solution, mixing thoroughly and standing for removing large-grain sediment, to obtain a suspension.

In some embodiments of the above-mentioned aspects, the culturing of the suspension on the enrichment medium added with ethylene oxide and the culturing of the bacteria having a potential for degrading ethylene oxide on the purification medium may be anaerobic culturing or aerobic culturing.

In some embodiments of the above-mentioned aspects, the enrichment medium added with ethylene oxide may be added with 100 mg/L of ethylene oxide.

In some embodiments of the above-mentioned aspects, the enrichment medium may be selected from one of:

tryptone soybean broth medium, consisting of the following: 17 parts of tryptone, 3 parts of soy peptone, 5 parts of sodium chloride, 2.5 parts of dipotassium phosphate, 2.5 parts of glucose, with pH adjusted to 7.0-7.5 and the volume adjusted with water to 1000 parts;

0.5% glucose broth medium, consisting of the following: 10 parts of peptone, 5 parts of sodium chloride, 5 parts of glucose, 3 parts of beef extract powder, with pH adjusted to 7.0-7.4 and the volume adjusted with water to 1000 parts;

Sabouraud glucose liquid medium, consisting of the following: 40 parts of glucose, 5 parts of casein tryptone, 5 parts of animal tissue pepsin digest, with pH adjusted to 5.4-5.8 and the volume adjusted with water to 1000 parts;

SCDLP liquid medium, consisting of the following: 17 parts of casein peptone, 3 parts of soy peptone, 5 parts of sodium chloride, 2.5 parts of dipotassium phosphate, 2.5 parts of glucose, 1 part of lecithin, with pH adjusted to 7.1-7.3 and the volume adjusted with water to 1000 parts;

beef broth peptone medium, consisting of the following: 3 parts of beef extract, 1 part of yeast extract, 5 parts of peptone, 10 parts of glucose, with pH adjusted to 6.8-7.3 and the volume adjusted with water to 1000 parts;

nutrient broth medium, consisting of the following: 10 parts of peptone, 3 parts of beef extract, 5 parts of sodium chloride, with pH adjusted to 7.0-7.6 and the volume adjusted with water to 1000 parts;

LB medium, consisting of the following: 10 parts of tryptone, 5 parts of yeast extract, 10 part of sodium chlorides, with pH adjusted to 6.8-7.5 and the volume adjusted with water to 1000 parts;

glucose peptone medium, consisting of the following: 5 parts of peptone, 5 parts of dipotassium phosphate, 5 parts of glucose, with pH adjusted to 7.1-7.5 and the volume adjusted with water to 1000 parts;

liquid medium A, consisting of the following: 10 parts of peptone, 1 part of yeast extract, 10 parts of glucose, 5 parts of sodium chloride, with pH adjusted to 6.8-7.2 and the volume adjusted with water to 1000 parts;

PY basic liquid medium, consisting of the following: 0.5 parts of tryptone, 0.5 parts of peptone, 1 part of yeast extract, 4 parts of saline solution, with pH adjusted to 6.8-7.2 and the volume adjusted with water to 1000 parts; wherein the saline solution consists of the following: 0.2 part of anhydrous calcium chloride, 1 part of monopotassium phosphate, 1 part of dipotassium phosphate, 0.48 parts of magnesium sulfate heptahydrate, 2 parts of sodium chloride and the volume adjusted with water to 1000 parts; and lactic acid bacteria liquid medium, consisting of the following: 20 parts of peptone, 10 parts of beef extract, 5 parts of yeast extract, 2 parts of ammonium citrate dibasic, 2 parts of dipotassium phosphate, 20 parts of glucose, 5 parts of sodium acetate, 0.58 parts of magnesium sulfate, 0.25 part of manganese sulfate, with pH adjusted to 6.2-6.6 and the volume adjusted with water to 1000 parts.

In some embodiments of the above-mentioned aspects, the purification medium may be prepared by adding agar and ethylene oxide in the enrichment medium. In some embodiments of the above-mentioned aspects, agar added may be 15 parts.

In some embodiments of the above-mentioned aspects, the culturing may be performed at 20-40° C.

In some embodiments of the above-mentioned aspects, the culturing may be performed for 24-48 hrs.

In another aspect of the present disclosure, there provides a method for manufacturing bacteria strains capable of tolerating and degrading ethylene oxide, comprising subjecting a bacteria having a potential for degrading ethylene oxide to ethylene oxide tolerance and degradation acclimatization, the ethylene oxide tolerance acclimatization and degradation acclimatization comprising:

ethylene oxide tolerance acclimatization: culturing the bacteria having a potential for degrading ethylene oxide sequentially on ethylene oxide tolerance acclimatization media containing a gradient of increasing concentrations of ethylene oxide; after each culturing, selecting a single colony having a largest radius for further culturing on an ethylene oxide tolerance acclimatization medium containing a next concentration in the gradient of ethylene oxide; and finally selecting a single colony having a largest radius on an ethylene oxide tolerance acclimatization medium containing a highest concentration in the gradient of ethylene oxide, to obtain an ethylene oxide-tolerant bacteria; and, culturing the ethylene oxide-tolerant bacteria sequentially on ethylene oxide degradation acclimatization media containing ethylene oxide and a gradient of decreasing concentrations of carbohydrate carbon source for culturing; after each culturing, selecting a single colony having a largest radius for further culturing on an ethylene oxide degradation acclimatization medium containing a next concentration in the gradient of carbohydrate carbon source; and finally, selecting a single colony having a largest radius on an ethylene oxide degradation acclimatization medium containing a lowest concentration in the gradient of carbohydrate carbon source, to obtain the bacteria capable of tolerating and degrading ethylene oxide.

In the ethylene oxide tolerance acclimatization medium, the concentrations of ethylene oxide are sequentially increased. Culturing on a medium containing a low concentration of ethylene oxide provides preliminary strains tolerant to the low concentration of ethylene oxide. After sequential inoculation and culturing on media containing increased concentrations of ethylene oxide, the tolerance of the strains to ethylene oxide is improved, and finally, ethylene oxide-tolerant bacteria is obtained.

The ethylene oxide-tolerant bacteria above obtained are inoculated and cultured on the ethylene oxide degradation acclimatization media containing decreasing concentrations of carbohydrate carbon source to induce the ethylene oxide-tolerant bacteria to use ethylene oxide as the only carbon source required for growth. When the concentration of carbohydrate carbon source is zero (0), ethylene oxide becomes the main carbon source for strain growth. The capability of the strains to degrade ethylene oxide is increased. Finally, strains capable of degrading ethylene oxide are obtained.

In some embodiments of the above-mentioned aspects, the ethylene oxide tolerance acclimatization medium may contain a gradient of increasing concentrations of ethylene oxide from 100 to 800 mg/L.

In some embodiments of the above-mentioned aspects, the ethylene oxide tolerance acclimatization medium may contain increasing concentrations of ethylene oxide of at least two of 0-100 mg/L, 100-200 mg/L, 200-500 mg/L, and 500-800 mg/L.

In some embodiments of the above-mentioned aspects, the ethylene oxide tolerance acclimatization medium may further contain a nitrogen source, a carbohydrate carbon source, and agar.

In some embodiments of the above-mentioned aspects, in the ethylene oxide tolerance acclimatization medium, the nitrogen source may be peptone, and/or the carbohydrate carbon source may be glucose.

In some embodiments of the above-mentioned aspects, the ethylene oxide tolerance acclimatization medium and/or the ethylene oxide degradation acclimatization medium may have a pH of, for example, 5.4-5.8.

In some embodiments of the above-mentioned aspects, the ethylene oxide degradation acclimatization medium may further contain a nitrogen source and agar, and the nitrogen source may be, for example, peptone.

In some embodiments of the above-mentioned aspects, the carbohydrate carbon source in the ethylene oxide degradation acclimatization medium may for example be glucose.

In some embodiments of the above-mentioned aspects, the ethylene oxide degradation acclimatization media may have decreasing concentrations of carbohydrate carbon source from 50% to 0%.

In some embodiments of the above-mentioned aspects, the gradient of decreasing concentrations of carbohydrate carbon source in the ethylene oxide degradation acclimatization media may be at least two concentrations selected from 100%-50%, 50%-30%, 30%-10%, and 10%-0%.

In some embodiments of the above-mentioned aspects, the ethylene oxide degradation acclimatization medium has a concentration of ethylene oxide that could be—the same as the highest concentration in the gradient of ethylene oxide in the ethylene oxide tolerance acclimatization medium.

In some embodiments of the above-mentioned aspects, the ethylene oxide tolerance acclimatization medium may consist of: 10 parts of peptone, 40 parts of glucose, agar 15 parts, pH adjusted to 5.4-5.8 and the volume adjusted with water to 1000 parts, and is then added with ethylene oxide of 100-800 mg/L.

In some embodiments of the above-mentioned aspects, the ethylene oxide degradation acclimatization medium may consist of: 10 parts of peptone, 0-20 parts of glucose, and 15 parts of agar, with pH adjusted to 5.4-5.8 and the volume adjusted with water to 1000 parts, and is then added with ethylene oxide added.

In some embodiments of the above-mentioned aspects, the culturing is performed at 20-40° C.

In some embodiments of the above-mentioned aspects, the culturing is performed for 24-48 hrs.

In another aspect of the present disclosure, there provides a method for screening or producing bacteria capable of degrading ethylene oxide, comprising: screening bacteria having a potential for degrading ethylene oxide according to the method mentioned above; and, subjecting the bacteria having a potential for degrading ethylene oxide to ethylene oxide tolerance and degradation acclimatization according to the method mentioned above.

In another aspect of the present disclosure, the degradation rate of ethylene oxide of the resulting strains is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of the strain.

Hereinafter, representative examples of screening and acclimatizing bacteria strains capable of degrading ethylene oxide are provided.

Example 1

1. Screening bacteria having a potential for degrading ethylene oxide:

(1). Preliminary Screening

The sludge samples of this example were taken from a sludge mixture at the drain outlet of a sewage treatment plant in a suburb of Guangzhou, Guangdong Province. The samples were placed in a glass vial, sealed and stored at a low temperature (ice pack in a foam box or refrigerator at 4° C.).

10.0 g of the sample was weighed, and 100 mL of 0.03 mol/L phosphate buffer was added. After mixing thoroughly and standing for 120 min, large-grain sediment was removed to obtain a suspension.

Enrichment medium was prepared, and ethylene oxide was added (the method is as described below).

1 mL of suspension was inoculated into 10 mL of enrichment medium added with ethylene oxide. This step was performed in duplicate, one was subjected to aerobic culturing at 37° C. for 24 h-48 h, and the other one was placed in a 2.5 L round-bottomed vertical anaerobic culture bag together with a 2.5 L anaerobic gas production bag (the culture bag is sealed) and subjected to anaerobic culturing at 37° C. for 24 h-48 h. Growth situation was observed. Dominant strains were selected to obtain bacteria having a potential for degrading ethylene oxide.

(2). Purification

The bacteria having a potential for degrading ethylene oxide obtained in the primary screening were inoculated on corresponding purification medium plates. This step was performed in duplicate, one was subjected to aerobic culturing at 37° C. for 24 h-48 h, and the other one was placed in a 2.5 L round-bottomed vertical anaerobic culture bag together with a 2.5 L anaerobic gas production bag (the culture bag is sealed) and subjected to anaerobic culturing at 37° C. for 24 h-48 h. Growth situation was observed.

Single colonies growing well on the purification medium plates were picked and inoculated into corresponding enrichment media for 24 h of culturing to obtained purified bacteria having a potential for degrading ethylene oxide, which were preserved in glycerine (the rate of the culture to 50% glycerine was 1:1) at −80° C.

The enrichment medium used in the primary screening and purification may be selected from one of:

tryptone soybean broth medium: tryptone 17 g, soy peptone 3 g, sodium chloride 5 g, dipotassium phosphate 2.5 g, glucose 2.5 g, pH adjusted to 7.0-7.5, and filled with distilled water to 1000 mL;

0.5% glucose broth medium: peptone 10 g, sodium chloride 5 g, glucose 5 g, beef extract powder 3 g, pH adjusted to 7.0-7.4, and filled with distilled water to 1000 mL;

Sabouraud glucose liquid medium: glucose 40 g, casein tryptone 5 g, animal tissue pepsin digest 5 g, pH adjusted to 5.4-5.8, and filled with distilled water to 1000 mL;

SCDLP liquid medium: casein peptone 17 g, soy peptone 3 g, sodium chloride 5 g, dipotassium phosphate 2.5 g, glucose 2.5 g, lecithin 1 g, pH adjusted to 7.1-7.3, and filled with distilled water to 1000 mL;

beef broth peptone medium: beef extract 3 g, yeast extract 1 g, peptone 5 g, glucose 10 g, pH adjusted to 6.8-7.3, and filled with distilled water to 1000 mL;

nutrient broth medium: peptone 10 g, beef extract 3 g, sodium chloride 5 g, pH adjusted to 7.0-7.6, and filled with distilled water to 1000 mL;

LB medium: tryptone 10 g, yeast extract 5 g, sodium chloride 10 g, pH adjusted to 6.8-7.5, and filled with distilled water to 1000 mL;

glucose peptone medium: peptone 5 g, dipotassium phosphate 5 g, glucose 5 g, pH adjusted to 7.1-7.5, and filled with distilled water to 1000 mL;

liquid medium A: peptone 10 g, yeast extract 1 g, glucose 10 g, sodium chloride 5 g, pH adjusted to 6.8-7.2, and filled with distilled water to 1000 mL;

PY basic liquid medium: tryptone 0.5 g, peptone 0.5 g, yeast extract 1 g, saline solution 4 mL, pH adjusted to 6.8-7.2, and filled with distilled water to 1000 mL; the saline solution consists of: anhydrous calcium chloride 0.2 g, monopotassium phosphate 1 g, dipotassium phosphate 1 g, magnesium sulfate heptahydrate 0.48 g, sodium chloride 2 g, and filled with distilled water to 1000 mL; and lactic acid bacteria liquid medium: peptone 20 g, beef extract 10 g, yeast extract 5 g, ammonium citrate dibasic 2 g, dipotassium phosphate 2 g, glucose 20 g, sodium acetate 5 g, magnesium sulfate 0.58 g, manganese sulfate 0.25 g, pH adjusted to 6.2-6.6, and filled with distilled water to 1000 mL.

The enrichment medium added with ethylene oxide was prepared as follows:

The enrichment medium was prepared and distributed into 500 mL conical flasks (250 mL for each). Then, sterilization was performed at 121° C. for 20 min. Thereafter, the temperature was cooled down to room temperature. Pure ethylene oxide agent (100 ml ampoule containing pure ethylene oxide was previously store at −20° C. in a refrigerator for 48 h, an opening mark was made on the neck of the ampoule with a grinding wheel, and replaced in a refrigerator and store at −20° C. for 72 h. Then, ethylene oxide was removed and distributed into 10 ml brown bottles for use) was placed on an ice box. 28 μL of liquid ethylene oxide was injected by using a 100 µL sealed syringe into the sterilized medium, to obtained enrichment medium added with ethylene oxide, which was distributed into tubes (10 mL for each) for use.

The purification medium plate used in the purification step was prepared as follows:

Enrichment medium added with 15 g of agar but no ethylene oxide was distributed into 500 mL conical flasks (250 mL for each). Then, sterilization was performed at 121° C. for 20 min. when the temperature of the medium was cooled down to 50-56° C., an ice box was taken out from a refrigerator, and reagent pure ethylene oxide was placed on the ice box. 28 µL of liquid ethylene oxide was injected by using a 100 µL sealed syringe into the sterilized medium, to obtain a corresponding purification medium, which was made into plates (20 mL for each) for use.

2. Identification of the Strains

The single colonies of the purified bacteria having a potential for degrading ethylene oxide were selected and identified. Methods for identifying the strains were:

Morphologic identification: observation of the morphology of colonies, microscopic observation of the morphology of bacterial bodies, and identification of cultural features and Gram staining;

Physiological and biochemical identification: physicochemical properties including nutritional type, availability for nitrogen source and carbon source, biochemical tests, and the like; and The DNA in the genome that produces the ribosomal RNA is called the "rRNA gene" or simply "rDNA". Molecular biological identification: bacteria culturing, extraction of bacteria DNA, PCR amplification, 16s rRNA gene sequencing and sequence alignment analysis, which were sequentially performed.

Forward primer 27F: 5'-AGAGTTTGATCCTGGCTCAG-3' (SEQ ID NO: 1);

Reverse primer 1492R: 5'-GGTTACCTTGTTACGACTT-3' (SEQ ID NO: 2);

The obtained sequences of 16S rDNA of the bacteria strains were subjected to BLAST nucleotide sequence alignment, the result of which was used, in combination with the morphologic identification and the physiological and biochemical identification, to determine the species of the strains.

The purified bacteria having a potential for degrading ethylene oxide were identified as *Acetobacter peroxydans, Lactobacillus fermentum, Klebsiella pneumoniae, Bacillus subtilis, Enterococcus faecium, Alcaligenes faecalis, Proteus mirabilis, Lactobacillus* sp., and *Morganella morganii*, respectively. as shown in Table 1.

3. Ethylene Oxide Tolerance Acclimatization

Ethylene oxide tolerance acclimatization medium plates were made as follows: Peptone 10 g, glucose 40 g, agar 15 g, pH adjusted to 5.4-5.8, and filled with distilled water to 1000 mL which was distributed into 250 mL. Sterilization was then performed at 121° C. for 20 min. The medium was heated to melt before use. When the temperature of the medium was cooled down to 50-56° C., 25 mg, 50 mg, 125 mg, and 200 mg of ethylene oxide was added, respectively, by using a sealed injection needle to obtain four ethylene oxide tolerance acclimatization medium plates containing different concentrations of ethylene oxide (100 mg/L, 200 mg/L, 500 mg/L, and 800 mg/L, respectively), named as ethylene oxide tolerance acclimatization medium plate A, ethylene oxide tolerance acclimatization medium plate B, ethylene oxide tolerance acclimatization medium plate C, and ethylene oxide tolerance acclimatization medium plate D, respectively.

The purified bacteria having a potential for degrading ethylene oxide were streak-inoculated on ethylene oxide tolerance acclimatization medium A, and cultured at a constant temperature of 37° C. for 48 h; a single colony having a largest radius was picked for further inoculation on ethylene oxide tolerance acclimatization medium B, and cultured at a constant temperature of 37° C. for 48 h; a single colony having a largest radius was picked for further inoculation on ethylene oxide tolerance acclimatization medium C, and cultured at a constant temperature of 37° C. for 48 h; a single colony having a largest radius was picked for further inoculation on ethylene oxide tolerance acclimatization medium D, and cultured at a constant temperature of 37° C. for 48 h, to obtain ethylene oxide-tolerant bacteria. Growth situation of the strains on the ethylene oxide tolerance acclimatization medium plates A, B, C, and D are as shown in Table 1.

4. Ethylene Oxide Degradation Acclimatization:

Ethylene oxide degradation acclimatization medium plates were made as follows: Peptone 10 g, glucose (20 g, 12 g, 4 g, and 0 g, respectively), agar 15 g, pH adjusted to 5.4-5.8, and filled with distilled water to 1000 mL which was distributed into 250 mL. Sterilization was then performed at 121° C. for 20 min. The medium was heated to melt before use. When the temperature of the medium was cooled down to 50-56° C., 200 mg of ethylene oxide was added by using a sealed injection needle to obtain four ethylene oxide degradation acclimatization medium plates containing different concentrations of carbon source (50%, 30%, 10%, 0%, respectively), named as ethylene oxide degradation acclimatization medium plate A, ethylene oxide degradation acclimatization medium plate B, ethylene oxide degradation acclimatization medium plate C, and ethylene oxide degradation acclimatization medium plate D, respectively.

The ethylene oxide-tolerant bacteria were streak-inoculated on Ethylene Oxide Degradation Acclimatization medium A, and cultured at a constant temperature of 37° C. for 48 h; a single colony having a largest radius was picked for further inoculation on Ethylene Oxide Degradation Acclimatization medium B, and cultured at a constant temperature of 37° C. for 48 h; a single colony having a largest radius was picked for further inoculation on Ethylene Oxide Degradation Acclimatization medium C, and cultured at a constant temperature of 37° C. for 48 h; a single colony having a largest radius was picked for further inoculation on Ethylene Oxide Degradation Acclimatization medium D, and cultured at a constant temperature of 37° C. for 48 h; a single colony having a largest radius was picked and preserved on an agar medium bevel containing corresponding nutritional components in Ethylene Oxide Degradation Acclimatization medium D, to obtain ethylene oxide-degrading strains. Growth situation of the strains on the ethylene oxide degradation acclimatization medium plates A, B, C, and D are as shown in Table 1.

5. Identification of the Degradation of Ethylene Oxide by the Strains

The bacteria having a potential for degrading ethylene oxide which have not been subjected to the acclimatization steps and the strains capable of tolerating and degrading ethylene oxide obtained after the acclimatization steps were inoculated into activation medium, respectively, for activation, and cultured to a bacteria concentration of $10^{10}$-$10^{12}$ cfu/mL in the culture.

The activation medium was made as follows: Peptone 10 g, filled with distilled water to 1000 mL which was distributed into 400 mL. Then, sterilization was performed at 121° C. for 20 min. Thereafter, the temperature of the medium was cooled down to RT for storage. 160 mg and 320 mg of ethylene oxide was added, respectively, by using a sealed syringe to obtain two activation media containing different concentrations (400 mg/L and 800 mg/L, respectively) of ethylene oxide for the test of degrading capability of the ethylene oxide-degrading strains.

Comparative experiment for the degradation of ethylene oxide was performed with the following test groups and control group.

Test group 1: 5 mL of an activation culture of the bacteria capable of tolerating and degrading ethylene oxide was inoculated into 400 mL of activation media containing 400 mg/L (1A) and 800 mg/L (1B), respectively, of ethylene oxide. The amount of live bacteria in the medium was $10^8$-$10^{10}$ cfu/mL.

Test group 2: 5 mL of an activation culture of the bacteria having a potential for degrading ethylene oxide which have not been subjected to the acclimatization steps was inoculated into 400 mL of activation media containing 400 mg/L (2A) and 800 mg/L (2B), respectively, of ethylene oxide. The amount of live bacteria in the medium was $10^8$-$10^{10}$ cfu/mL.

Control group: 400 mL of activation media containing 400 mg/L (control group A) and 800 mg/L (control group B), respectively, of ethylene oxide with no bacteria strain inoculated.

The test groups and control groups are placed together in an incubated for culturing at 37° C. for 48 h. For anaerobic bacteria, the plates inoculated with the strains were placed in a 2.5 L round-bottomed vertical anaerobic culture bag together with a 2.5 L anaerobic gas production bag (the culture bag is sealed) and subjected to anaerobic culturing at 37° C. The result of degradation was detected by gas chromatography.

The test samples and the control samples were sent to the CDC of Shaanxi Province for gas chromatography assay to calculate the concentration of residual ethylene oxide and the rate of degradation of ethylene oxide in the sample. Detection is performed according to the methods described in "Sanitary Standards for Disposable Hygiene Products" (GB15979-2002) of China National Standards as follows:

a series of ethylene oxide standards of 0-200 mg/L concentrations were made by taking a certain volume of pure ethylene oxide gas with a sealed syringe for dissolving in deionized water;

the subject samples to be analyzed were prepared by diluting samples from the treatment and control groups 5 times with deionized water;

after the GC instrument is stabilized and under the same conditions, 2 μL each of the ethylene oxide standards and the diluted samples to be analyzed were injected into the GC instrument, wherein each sample was measured twice in parallel;

qualitive determination was conducted according to the retention time and quantitative calculation on each peak area was performed to take the average value;

an ethylene oxide standard curve was plotted according to the measurement data of the ethylene oxide standards, and the concentrations of residual ethylene oxide within each sample from the control and treatment groups were found based on the peak area corresponding to ethylene oxide thereof; and the degradation rate of ethylene oxide for each sample was calculated according to the following formula: Degradation Rate (%)=(Control Group Concentration−Treatment Group Concentration)/Control Group Concentration×100.

Other details of the experiment include Column: Chromosorb 101HP60-80 mesh, glass column 2 m long, diameter 3 mm. Column temperature: 120° C. Detector: 150° C., Gasifier: 150° C.; Carrier gas volume: Nitrogen: 35 ml/min, Hydrogen: 35 ml/min, Air: 350 ml/min, and the pre-column pressure is about 108 Kpaa.

Results of the degradation of ethylene oxide for the strains are shown in Table 1.

TABLE 1

Results of identification, acclimatization, degradation comparison of bacteria having a potential for degrading ethylene oxide.

| Strain Name | Nutrition type | Medium | C (100%)/EO (mg/L) | | | | EO (800 mg/L)/C (%) | | | | EO (800 mg/L) + C (0%) Degradation rate (%) | | EO (400 mg/L) + C (0%) Degradation rate (%) | |
|---|---|---|---|---|---|---|---|---|---|---|---|---|---|---|
| | | | 100 | 200 | 500 | 800 | 50 | 30 | 10 | 0 | Before Acc. | After Acc. | Before Acc. | After Acc. |
| A. peroxydans | Aerobic | Tryptone soybean broth | + | + | + | + | + | + | + | ± | 5.97% | 51.28% | 15.33% | 63.82% |
| L. fermentum | Amphitrophic | Sabouraud glucose | + | + | + | + | + | + | + | ± | 6.09% | 52.54% | 19.63% | 83.93% |
| K. pneumoniae | Amphitrophic | 0.5% glucose broth | + | + | + | + | + | + | + | + | 6.63% | 54.35% | 16.52% | 64.67% |
| B. subtilis | Aerobic | 0.5% glucose broth | + | + | + | + | + | + | + | + | 8.86% | 57.19% | 17.40% | 72.96% |
| E. faecium | Amphitrophic | Tryptone soybean broth | + | + | + | + | + | + | + | ± | 5.90% | 51.45% | 16.77% | 67.26% |
| A. faecalis | Aerobic | Sabouraud glucose | + | + | + | + | + | + | + | + | 10.02% | 68.65% | 20.60% | 92.90% |

TABLE 1-continued

Results of identification, acclimatization, degradation comparison of bacteria having a potential for degrading ethylene oxide.

| Strain Name | Nutrition type | Medium | C (100%)/ EO (mg/L) | | | | EO (800 mg/L)/C (%) | | | | EO (800 mg/L) + C (0%) Degradation rate (%) | | EO (400 mg/L) + C (0%) Degradation rate (%) | |
|---|---|---|---|---|---|---|---|---|---|---|---|---|---|---|
| | | | 100 | 200 | 500 | 800 | 50 | 30 | 10 | 0 | Before Acc. | After Acc. | Before Acc. | After Acc. |
| P. mirabilis | Amphi-trophic | Tryptone soybean broth | + | + | + | + | + | + | + | + | 6.11% | 60.23% | 17.66% | 75.45% |
| Lactobacillus sp. | Amphi-trophic | 0.5% glucose broth | + | + | + | + | + | + | + | ± | 7.04% | 61.76% | 18.12% | 77.16% |
| M. morganii | Amphi-trophic | Tryptone soybean broth | + | + | + | + | + | + | + | + | 5.84% | 58.56% | 16.84% | 72.88% |

Note:
+ normal growth; ± low growth.

According to the characterization results of morphology, physiology, biochemistry, and molecular biology, EO-degrading potential bacteria strains obtained by screening and purification according to Example 1 and reported in Table 1 were as follows:

*Alcaligenes faecalis* strain EO-05 with the Deposit number of CGMCC No. 18435;

*Alcaligenes faecalis* strain comprising the 16S rDNA sequence of SEQ ID NO: 3;

*Acetobacter peroxydans* EO-01 strain with Deposit number of CGMCC No. 18431;

*Acetobacter peroxydans* strain comprising the 16S rDNA sequence of SEQ ID NO: 4;

*Lactobacillus fermentum* EO-02 strain with Deposit number of CGMCC No. 18432;

*Lactobacillus fermentum* strain comprising the 16S rDNA sequence of SEQ ID NO: 5;

*Bacillus subtilis* EO-03 strain with Deposit number of CGMCC No. 18433; and

*Bacillus subtilis* strain comprising the 16S rDNA sequence of SEQ ID NO: 6.

Example 2

The samples of this Example were taken from a sludge mixture at the drain outlet of a chemical plant in Foshan, Guangdong Province. The screening, identification, acclimatization, and ethylene oxide degradation comparison steps are the same as those in Example 1.

The purified bacteria having a potential for degrading ethylene oxide were identified as *Pseudomonas aeruginosa*, *Pseudomonas otitidis*, *Kurthia gibsonii*, *Klebsiella pneumoniae*, *Escherichia coli*, *Enterobacter roggenkampii*, *Enterococcus faecium*, *Cronobacter sakazakii*, *Clostridium scatologenes*, *Clostridium acidisoli*, *Clostridium kogasensis*, and *Enterococcus hirae*, respectively.

Results of ethylene oxide degradation comparison experiments of the strains are shown in Table 2.

TABLE 2

Results of identification, acclimatization, degradation comparison of bacteria having a potential for degrading ethylene oxide.

| Strain Name | Medium | C(100%)/ EO(mg/L) | | | | EO(800 g/L)/ C(%) | | | | EO(800 mg/L)/C(0%) Degradation rate(%) | | EO(400 mg/L)/C(0%) Degradation rate(%) | |
|---|---|---|---|---|---|---|---|---|---|---|---|---|---|
| | | 100 | 200 | 500 | 800 | 50 | 30 | 10 | 0 | Before Acc. | After Acc. | Before Acc. | After Acc. |
| P. aeruginosa | Nutrient broth | + | + | + | + | + | + | + | ± | 6.84% | 64.26% | 15.88% | 68.79% |
| P. otitidis | Nutrient broth | + | + | + | + | + | + | + | ± | 6.39% | 62.71% | 15.42% | 67.87% |
| K. gibsonii | Glucose peptone | + | + | + | + | + | + | + | + | 9.41% | 67.82% | 18.35% | 80.85% |
| E. coli | LB | + | + | + | + | + | + | + | + | 8.22% | 67.56% | 17.63% | 75.41% |
| E. hirae | beef broth peptone | + | + | + | + | + | + | + | ± | 5.44% | 50.22% | 16.57% | 65.27% |
| E. faecium | Glucose peptone | + | + | + | + | + | + | + | ± | 5.56% | 50.13% | 15.38% | 66.32% |
| C. sakazakii | LB | + | + | + | + | + | + | + | + | 7.15% | 63.43% | 15.98% | 66.38% |
| C. scatologenes | Glucose peptone | + | + | + | + | + | + | − | − | 18.62% | 91.70% | 19.06% | 83.61% |
| C. acidisoli | Beef broth peptone | + | + | + | + | + | + | ± | ± | 6.06% | 51.64% | 19.73% | 84.19% |

TABLE 2-continued

Results of identification, acclimatization, degradation comparison of
bacteria having a potential for degrading ethylene oxide.

| Strain Name | Medium | C(100%)/ EO(mg/L) | | | | EO(800 g/L)/ C(%) | | | | EO(800 mg/L)/C(0%) Degradation rate(%) | | EO(400 mg/L)/C(0%) Degradation rate(%) | |
|---|---|---|---|---|---|---|---|---|---|---|---|---|---|
| | | 100 | 200 | 500 | 800 | 50 | 30 | 10 | 0 | Before Acc. | After Acc. | Before Acc. | After Acc. |
| E. roggen-kampii | Beef broth peptone | + | + | + | + | + | + | ± | ± | 6.31% | 53.44% | 18.28% | 83.75% |
| K. pneumoniae | Beef broth peptone, Nutrient broth | + | + | + | + | + | + | + | + | 6.12% | 53.42% | 15.95% | 64.18% |

Note:
+ normal growth; ± Low growth; − no growth; wherein EO-08 strain degradation medium contains 30% of carbon source.

According to the characterization results of morphology, physiology, biochemistry, and molecular biology, EO-degrading potential bacteria strains obtained by screening and purification according to Example 2 and reported in Table 2 were as follows:

*Kurthia gibsonii* strain EO-06 with Deposit number of CGMCC No. 18436;

*Kurthia gibsonii* strain comprising the 16S rDNA sequence of SEQ ID NO: 7;

*Clostridium acidisoli* strain EO-09 with Deposit number of CGMCC No. 18439;

*Clostridium acidisoli* strain comprising the 16S rDNA sequence of SEQ ID NO: 8;

*Enterococcus faecium* EO-04, with the Deposit number CGMCC No. 18434;

*Enterococcus faecium* strain comprising the 16S rDNA sequence of SEQ ID NO: 9;

*Enterococcus azikeevi* EO-07, with the Deposit number CGMCC No. 18437;

*Enterococcus azikeevi* strain comprising the 16S rDNA sequence of SEQ ID NO: 10;

*Enterobacter roggenkampii* EO-10, with the Deposit number CGMCC No. 18440;

*Enterobacter roggenkampii* strain comprising the 16S rDNA sequence of SEQ ID NO: 11; and

*Clostridium kogasensis* strain EO-08 with the Deposit number of CGMCC No. 18438 or a *Clostridium kogasensis* strain comprising the 16S rDNA sequence of SEQ ID NO. 12.

Example 3

The samples of this Example were taken from a sludge mixture at the drain outlet of a sewage treatment plant in Xi'an, Shaanxi Province. The screening, identification, acclimatization, and ethylene oxide degradation comparison steps are the same as those in Example 1.

The purified bacteria having a potential for degrading ethylene oxide were identified as *Pseudomonas fluorescens, Rhodospirillum rubrum, Lactobacillus, Lactococcus lactis, Acetobacter, Enterococcus faecium, Nitrobacter, Mycobacterium, Sphingomonas, Flavobacterium, Escherichia coli, Bacillus subtilis* and *Klebsiella pneumoniae*, respectively.

Results of ethylene oxide degradation comparison experiments of the strains are shown in Table 3.

TABLE 3

Results of identification, acclimatization, degradation comparison of
bacteria having a potential for degrading ethylene oxide.

| Strain Name | Nutrition type | Medium | C (100%)/ EO(mg/L) | | | | EO (800 mg/L)/ C (%) | | | | EO (800 mg/L)/ C (0%) Degradation rate (%) | | EO (400 mg/L) /C (0%) Degradation rate ( % ) | |
|---|---|---|---|---|---|---|---|---|---|---|---|---|---|---|
| | | | 100 | 200 | 500 | 800 | 50 % | 30 % | 10 % | 0 % | Before Acc. | After Acc. | Before Acc. | After Acc. |
| P. fluorescens | Aerobic | A | + | + | + | + | + | + | + | ± | 6.21% | 60.31% | 16.84% | 70.72% |
| R. rubrum | Amphitrophic | PY basic | + | + | + | + | + | + | + | ± | 6.13% | 58.71% | 14.42% | 64.87% |
| B. mutans | Amphitrophic | Lactic acid bacteria medium | + | + | + | + | + | + | + | + | 7.02% | 65.22% | 16.67% | 76.23% |
| L. llactis | Amphitrophic | Lactic acid bacteria medium | + | + | + | + | + | + | + | ± | 5.96% | 59.47% | 15.54% | 64.23% |
| Acetobacter | Aerobic | PY basic | + | + | + | + | + | + | + | ± | 5.48% | 52.63% | 15.22% | 63.14% |
| Nitrobacter | Aerobic | PY basic | + | + | + | + | + | + | ± | ± | 5.15% | 50.79% | 14.17% | 63.51% |

TABLE 3-continued

Results of identification, acclimatization, degradation comparison of bacteria having a potential for degrading ethylene oxide.

| Strain Name | Nutrition type | Medium | C (100%)/ EO(mg/L) | | | | EO (800 mg/L)/ C (%) | | | | EO (800 mg/L)/ C (0%) Degradation rate (%) | | EO (400 mg/L) /C (0%) Degradation rate (%) | |
|---|---|---|---|---|---|---|---|---|---|---|---|---|---|---|
| | | | 100 | 200 | 500 | 800 | 50 % | 30 % | 10 % | 0 % | Before Acc. | After Acc. | Before Acc. | After Acc. |
| *Mycobacterium* | Aerobic | A | + | + | + | + | + | + | + | ± | 7.54% | 67.27% | 18.86% | 86.45% |
| *Sphingomonas* | Amphi-trophic | Lactic acid bacteria medium | + | + | + | + | + | + | + | + | 11.35% | 71.46% | 22.68% | 90.48% |
| *Flavo-bacterium* | Aerobic | PY basic | + | + | + | + | + | + | + | ± | 7.26% | 68.51% | 16.82% | 82.66% |
| *B. subtilis* | Aerobic | PY basic | + | + | + | + | + | + | + | + | 8.24% | 60.32% | 16.92% | 74.48% |
| *Lactobacillus* | An-aerobic | Lactic acid bacteria medium | + | + | + | + | + | + | + | + | 6.89% | 64.83% | 17.32% | 75.96% |
| *K. pneumoniae* | Amphi-trophic | A | + | + | + | + | + | + | + | + | 6.51% | 54.89% | 16.95% | 65.21% |
| *E. coli* | Amphi-trophic | A | + | + | + | + | + | + | + | + | 7.72% | 66.86% | 17.11% | 76.81% |

Note:
+ normal growth; ± Low growth.

Although the disclosure is illustrated and described herein with reference to specific examples, the disclosure is not intended to be limited to the details shown in any way. Rather, a person skilled in the art will understand that variations and modifications may be made in the details within the range of equivalents of the claims and without departing from the scope and spirit of the disclosure. Therefore, the scope of the present disclosure should only be defined by the claims attached herein.

What is claimed is:

1. A method for manufacturing bacteria strains capable of tolerating and degrading ethylene oxide, comprising subjecting a bacteria having a potential for degrading ethylene oxide to ethylene oxide tolerance acclimatization and degradation acclimatization, wherein the ethylene oxide tolerance acclimatization and degradation acclimatization comprises:
- culturing the bacteria having a potential for degrading ethylene oxide sequentially on a series of ethylene oxide tolerance acclimatization media containing a gradient of increasing concentrations of ethylene oxide; after each culturing on a single ethylene oxide tolerance acclimatization medium containing a concentration in the gradient of ethylene oxide, selecting a single colony having a largest radius for further culturing on an ethylene oxide tolerance acclimatization medium containing a next concentration in the gradient of ethylene oxide; and finally selecting a single colony having a largest radius on an ethylene oxide tolerance acclimatization medium containing a highest concentration in the gradient of ethylene oxide, to obtain an ethylene oxide-tolerant bacteria; and,
- culturing the ethylene oxide-tolerant bacteria sequentially on a series of ethylene oxide degradation acclimatization media containing ethylene oxide and a gradient of decreasing concentrations of carbohydrate carbon source for culturing; after each culturing on a single ethylene oxide degradation acclimatization medium containing a concentration in the gradient of carbohydrate source, selecting a single colony having a largest radius for further culturing on an ethylene oxide degradation acclimatization medium containing a next concentration in the gradient of carbohydrate carbon source; and finally, selecting a single colony having a largest radius on an ethylene oxide degradation acclimatization medium containing a lowest concentration in the gradient of carbohydrate carbon source, to obtain the bacteria capable of tolerating and degrading ethylene oxide.

2. The method of claim 1, wherein the ethylene oxide tolerance acclimatization medium comprises a gradient of increasing concentrations of ethylene oxide from 100 to 800 mg/L.

3. The method of claim 1, wherein the ethylene oxide tolerance acclimatization medium further comprises a nitrogen source, a carbohydrate carbon source, and agar.

4. The method of claim 1, wherein the ethylene oxide tolerance acclimatization medium and/or the ethylene oxide degradation acclimatization medium has a pH of 5.4-5.8.

5. The method of claim 1, wherein the ethylene oxide tolerance acclimatization medium consists of 10 parts of peptone, 40 parts of glucose, and 15 parts of agar, with pH adjusted to 5.4-5.8 and the volume adjusted with water to 1000 parts, and is then added with ethylene oxide of 100-800 mg/L.

6. The method of claim 1, wherein the ethylene oxide degradation acclimatization medium further comprises a nitrogen source and agar.

7. The method of claim 1, wherein the ethylene oxide degradation acclimatization medium has a gradient of decreasing concentrations of carbohydrate carbon source from 50% to 0%.

8. The method of claim 1, wherein the ethylene oxide degradation acclimatization medium has a concentration of ethylene oxide that is the same as the highest concentration in the gradient of ethylene oxide in the ethylene oxide tolerance acclimatization medium.

9. The method of claim 1, wherein the ethylene oxide degradation acclimatization medium consists of 10 parts of peptone, 0-20 parts of glucose, and 15 parts of agar, with pH adjusted to 5.4~5.8 and the volume adjusted with water to 1000 parts, and is then added with ethylene oxide.

10. The method of claim 1, wherein the culturing is performed at 20-40° C.

11. A method for screening or producing bacteria capable of degrading ethylene oxide, comprising:
- screening bacteria having a potential for degrading ethylene oxide a method comprising collecting a sludge having microbial activity, treating the sludge to obtain a suspension, providing an enrichment medium, and culturing the suspension in the enrichment medium added with ethylene oxide, to obtain strains having a potential for degrading ethylene oxide; and,
- culturing the potential strains on a purification medium, and selecting a single colony having a largest radius for further culturing on the enrichment medium with no ethylene oxide added, to obtain bacteria having a potential for degrading ethylene oxide; and
- subjecting the bacteria having a potential for degrading ethylene oxide to ethylene oxide tolerance and degradation acclimatization according to the method of claim 1.

* * * * *